US012800564B2

(12) United States Patent
Wu et al.

(10) Patent No.: US 12,800,564 B2
(45) Date of Patent: Nov. 17, 2026

(54) METHOD FOR INVERSE TRACEABILITY OF NON-POINT SOURCE POLLUTION IN WATERSHED AND COMPUTER DEVICE

(71) Applicant: Zhejiang A&F University, Hangzhou City (CN)

(72) Inventors: Jianhong Wu, Hangzhou City (CN); Qing Gui, Hangzhou City (CN); Ziqing Yang, Hangzhou City (CN); Jiani Xu, Hangzhou City (CN); Jun Lv, Hangzhou City (CN)

(73) Assignee: Zhejiang A&F University, Hangzhou City (CN)

( * ) Notice: Subject to any disclaimer, the term of this patent is extended or adjusted under 35 U.S.C. 154(b) by 360 days.

(21) Appl. No.: 18/781,760

(22) Filed: Jul. 23, 2024

(65) Prior Publication Data

US 2025/0164456 A1 May 22, 2025

(30) Foreign Application Priority Data

Nov. 18, 2023 (CN) ......................... 202311540143.7

(51) Int. Cl.
*G01N 33/18* (2006.01)
*G06N 7/01* (2023.01)

(52) U.S. Cl.
CPC ........... *G01N 33/1826* (2013.01); *G06N 7/01* (2023.01)

(58) Field of Classification Search
None
See application file for complete search history.

(56) References Cited

U.S. PATENT DOCUMENTS

2014/0129198 A1* 5/2014 Eddy ...................... G01V 20/00 703/9

FOREIGN PATENT DOCUMENTS

CN 106875032 A * 6/2017 ......... G06Q 10/0639
CN 115049210 A * 9/2022 ......... G06Q 10/0635

OTHER PUBLICATIONS

Liu Y, Yang C, Yu X, Wang M, Qi W. Monitoring the Landscape Pattern and Characteristics of Non-Point Source Pollution in a Mountainous River Basin. Int J Environ Res Public Health. Oct. 20, 2021;18(21):11032. doi: 10.3390/ijerph182111032. PMID: 34769560; PMCID: PMC8582686. (Year: 2021).*

* cited by examiner

*Primary Examiner* — Suman K Nath
*Assistant Examiner* — Alex T Devito
(74) *Attorney, Agent, or Firm* — Thompson Coburn LLP; Steven M. Ritchey

(57) ABSTRACT

A method for inverse traceability of non-point source pollution in a watershed and a computer device are provided. The method includes: acquiring basic data of a studied watershed; determining a location-weighted landscape contrast index (LWLI) of each landscape type in the studied watershed and a pollutant load of the studied watershed in a predetermined time cycle according to the basic data; and determining, according to the pollutant load and the LWLI, based on a pre-constructed pollution traceability model, an amount of non-point source pollutants entering a river for each landscape type in the studied field.

20 Claims, 11 Drawing Sheets

METHOD FOR INVERSE TRACEABILITY OF NON-POINT SOURCE POLLUTION IN WATERSHED AND COMPUTER DEVICE

CROSS-REFERENCE TO RELATED APPLICATION

This patent application claims the benefit and priority of Chinese Patent Application No. 202311540143.7 filed with the China National Intellectual Property Administration on Nov. 18, 2023, the disclosure of which is incorporated by reference herein in its entirety as part of the present application.

TECHNICAL FIELD

The present disclosure relates to the technical field of pollution analysis, and in particular, to a method for inverse traceability of non-point source pollution in a watershed and a computer device.

BACKGROUND

Conventional non-point source pollution traceability models can be divided into mechanism models and empirical models according to a complexity of modeling and a difference in adaptive spatial-temporal scale. The mechanism model is a relatively complete model system formed by combining a hydrological model, a soil erosion model and a pollutant migration and transformation model, such as a soil and water assessment tool (SWAT) model, an annualized agricultural non-point source pollution model (AnnAGNPS), and a spatially referenced regressions on watershed attributes (SPARROW) model. Although the mechanism model takes the law of pollutant migration and transformation into account, the application of this type of model needs a lot of data to calibrate and verify parameters of the model, which leads to certain limitations in application of the model.

The empirical model, also referred to as a "black box model", mainly uses regression analysis to establish a quantitative relationship between pollution sources and a monitoring section load, and an export coefficient model is the most widely used empirical model. When the export coefficient model is applied, a pollution discharge coefficient is directly applied to the export coefficient model. However, a pollutant load discharged from a "source" to an export watershed is related to a relative distance between a pollutant source and a watershed outlet, a relative elevation, a slope, and other factors. Therefore, results of pollutant loads at the watershed outlet calculated directly by means of an export coefficient cannot accurately reflect contributions of various pollution sources to water environment quality. A coupling model of a one-dimensional river water quality equation and the export coefficient is used to describe a process of pollutants from sink to source in a bottom-up manner, which overcomes subjectivity and uncertainty of directly using export coefficients of other regions, and is an effective means for traceability of non-point source pollution, but ignores an impact of a land-use spatial pattern on the export of non-point source pollution.

In related technologies, a constructed non-point source pollution traceability model cannot accurately simulate an impact of a landscape pattern on a non-point source pollution load in a watershed, which leads to uncertainty of model simulation results and inability to quantitatively evaluate contributions of different landscape types in the watershed to an amount of non-point source pollution entering a river, thereby limiting rational formulation of a non-point source pollution control scheme.

SUMMARY

A problem to be solved by the present disclosure is how to accurately trace a source of non-point source pollution in a watershed.

To resolve the above problem, in a first aspect, the present disclosure provides a method for inverse traceability of non-point source pollution in a watershed, including:

- acquiring basic data of a studied watershed, where the basic data comprises a digital elevation map, a land-use type map, hydrologic data, water quality data, and a weight and prior data of an export coefficient of each landscape type in the studied watershed, the landscape type comprises a source landscape and a sink landscape, where the source landscape represents a landscape type that acts as a pollution source in the studied watershed, and the sink landscape represents a landscape type that acts as a sink for pollutants in the studied watershed;
- determining a location-weighted landscape contrast index (LWLI) of each landscape type in the studied watershed and a pollutant load of the studied watershed in a predetermined time cycle according to the basic data, where the LWLI is used to indicate an impact of each landscape pattern on a migration process of non-point source pollutants, and the pollutant load comprises a pollutant load exported from the non-point source pollution to an outlet section of the studied watershed; and
- determining, according to the pollutant load and the LWLI, based on a pre-constructed pollution traceability model, an amount of the non-point source pollutants entering a river for each landscape type in the studied field, where the amount of the non-point source pollutants entering the river for each landscape type in the studied field represents an amount of pollutants exported by each landscape type and entering the river and is used to measure a contribution of each landscape type to non-point source pollution in the studied watershed.

In some embodiments, in the method for inverse traceability of non-point source pollution in the watershed, the determining an LWLI of each landscape type in the studied watershed according to the basic data comprises:

- calculating a relative distance-based LWLI, a relative elevation-based LWLI and a slope-based LWLI according to the basic data; and
- fusing the calculated relative distance-based LWLI, relative elevation-based LWLI and slope-based LWLI to obtain the LWLI.

In some embodiments, in the method for inverse traceability of non-point source pollution in the watershed, the calculating a relative distance-based LWLI, a relative elevation-based LWLI and a slope-based LWLI according to the basic data comprises:

- determining, according to the digital elevation map and land-use types, an area of each landscape type under corresponding distance, relative elevation or slope, and a cumulative percentage of the area;
- determining a Lorenz curve corresponding to each landscape type according to the cumulative percentage of the area; and determining the relative distance-based LWLI, the relative elevation-based LWLI and the slope-based LWLI based on the determined Lorenz curve and the weight.

In some embodiments, in the method for inverse traceability of non-point source pollution in the watershed, the determining the relative distance-based LWLI, the relative elevation-based LWLI and the slope-based LWLI based on the determined Lorenz curve and the weight of each landscape type comprises:

calculating by means of a following formula:

$$LWLI_{Relative\ distance/relative\ elevation/slope} = \frac{\sum_{i=1}^{m} A_{Sourcei} \times w_i \times AP_i}{\sum_{j=1}^{n} A_{Sinkj} \times w_j \times AP_j},$$

where m represents a total number of source landscapes in the studied watershed; n represents a total number of sink landscapes in the studied watershed; $A_{Source\ i}$ and $A_{Sink\ i}$ represent areas enclosed by Lorenz curves of an $i^{th}$ source landscape and a $j^{th}$ sink landscape in the studied watershed, respectively, and $AP_i$ and $AP_j$ represent area percentages of the $i^{th}$ source landscape and the $j^{th}$ sink landscape in the watershed, respectively; and $w_i$ and $w_j$ represent weights of the $i^{th}$ source landscape and the $j^{th}$ sink landscape, respectively.

In some embodiments, in the method for inverse traceability of non-point source pollution in the watershed, the fusing the calculated relative distance-based LWLI, relative elevation-based LWLI and slope-based LWLI to obtain the LWLI comprises:

using a quotient obtained by dividing a product of the relative distance-based LWLI and the relative elevation-based LWLI by the slope-based LWLI as the LWLI.

In some embodiments, in the method for inverse traceability of non-point source pollution in the watershed, the pre-constructed pollution traceability model is:

$$NS_g = \sum_{\eta=1}^{m+n} \left( \frac{f(Q_g)}{f(\overline{Q})} \right) e^{\eta} A_{\eta} LWLI \exp\left( -k \frac{T_g}{2} \right).$$

where $NS_g$ represents a pollutant load exported from a non-point source to the outlet section of the studied watershed in a $g^{th}$ time cycle; $\eta$ represents a number of land-use types, with a total of m+n; $\overline{Q}$ represents an average runoff flow rate in a predetermined time cycle; $Q_g$ represents a runoff flow rate in the $g^{th}$ time cycle; $f(\ )$ represents a functional relationship between a runoff flow rate at an outlet of the studied watershed and a pollutant load in runoff; $e^{\eta}$ represents a pollutant export coefficient of a $\eta^{th}$ land-use type; $A_{\eta}$ represents an area of the $\eta^{th}$ land-use type; a subscript g represents a $g^{th}$ time cycle; and k represents a first-order kinetic loss rate constant of river pollutants.

In some embodiments, in the method for inverse traceability of non-point source pollution in the watershed, the determining, according to the pollutant load and the LWLI, based on a pre-constructed pollution traceability model, an amount of the non-point source pollutants entering a river for each landscape type in the studied field comprises:

determining, according to the pollutant load and the LWLI, based on the pre-constructed pollution traceability model, parameter to be determined in the pollution traceability model by using a Bayesian inversion algorithm, where the parameter to be determined comprises a pollutant export coefficient corresponding to each land-use type; and determining an amount of non-point source pollutants entering the river for each land-use type in the studied field according to the pollutant export coefficient corresponding to each land-use type.

In some embodiments, in the method for inverse traceability of non-point source pollution in the watershed, the determining an amount of non-point source pollutants entering a river for each land-use type in the studied field according to the pollutant export coefficient corresponding to each land-use type comprises:

using a product of a pollutant export coefficient corresponding to each land-use type and the area, the LWLI and a runoff correction coefficient as an amount of non-point source pollutants entering the river for each land-use type.

In some embodiments, in the method for inverse traceability of non-point source pollution in the watershed, the determining a pollutant load of the studied watershed in a predetermined time cycle according to the basic data comprises:

determining the pollutant load of the studied watershed in the predetermined time cycle according to the basic data by using a LOADEST model; and determining whether the amount of the non-point source pollutants entering the river exceeds a predetermined threshold, and sending a single to an external device in response to a determination that the amount of the non-point source pollutants entering the river exceeds a predetermined threshold.

In some embodiments, in the method for inverse traceability of non-point source pollution in the watershed, the external device is an annunciator, which issues a warming in response to receiving the signal.

In some embodiments, in the method for inverse traceability of non-point source pollution in the watershed, the external device is an irrigation system, which, in response to receiving the signal, adjusts application rates of agricultural chemicals based on the amount of the non-point source pollutants entering the river.

In a second aspect, the present disclosure provides a computer device, comprising a memory, a processor, and a computer program stored in the memory and executable on the processor, where the processor, when executing the computer program, implements the method for inverse traceability of non-point source pollution in the watershed in the first aspect.

In a method for inverse traceability of non-point source pollution in the watershed and a computer device according to the present disclosure, during the process of tracing a source of non-point source pollution in a studied watershed, basic data in the studied watershed is acquired first, then a location-weighted landscape contrast index (LWLI) of each landscape type in the studied watershed and a pollutant load of the studied watershed in a predetermined time cycle are determined by means of the acquired basic data, and then according to the determined LWLI and pollutant load, an amount of pollutants entering a river, which represents a contribution of each landscape type to non-point source pollution in the studied watershed, is solved based on a pre-constructed pollution traceability model. That is, in the present disclosure, the determined LWLI included in the pollution traceability model can show an impact of each landscape pattern on a migration process of non-point source pollutants, and thus determined parameters are used to solve parameters in the pollution traceability model, which is conductive to accurately acquire parsing results of non-point source pollution sources in the watershed, quantitatively evaluate an amount of non-point source pollutants entering the river for different landscape types in the watershed, and effectively identify key pollution sources of non-point source pollution in the watershed, thereby providing effective guidance for control of non-point source pollution in the watershed, and having the characteristics of easy data acquisition and higher accuracy of obtained results, and the like. Therefore, the failure to fully consider the impact of a watershed landscape spatial structure on the non-point source pollution process in related technologies is avoided, and quantitative traceability of non-point source pollution in the watershed is achieved.

DETAILED DESCRIPTION OF THE EMBODIMENTS

Figure 1:
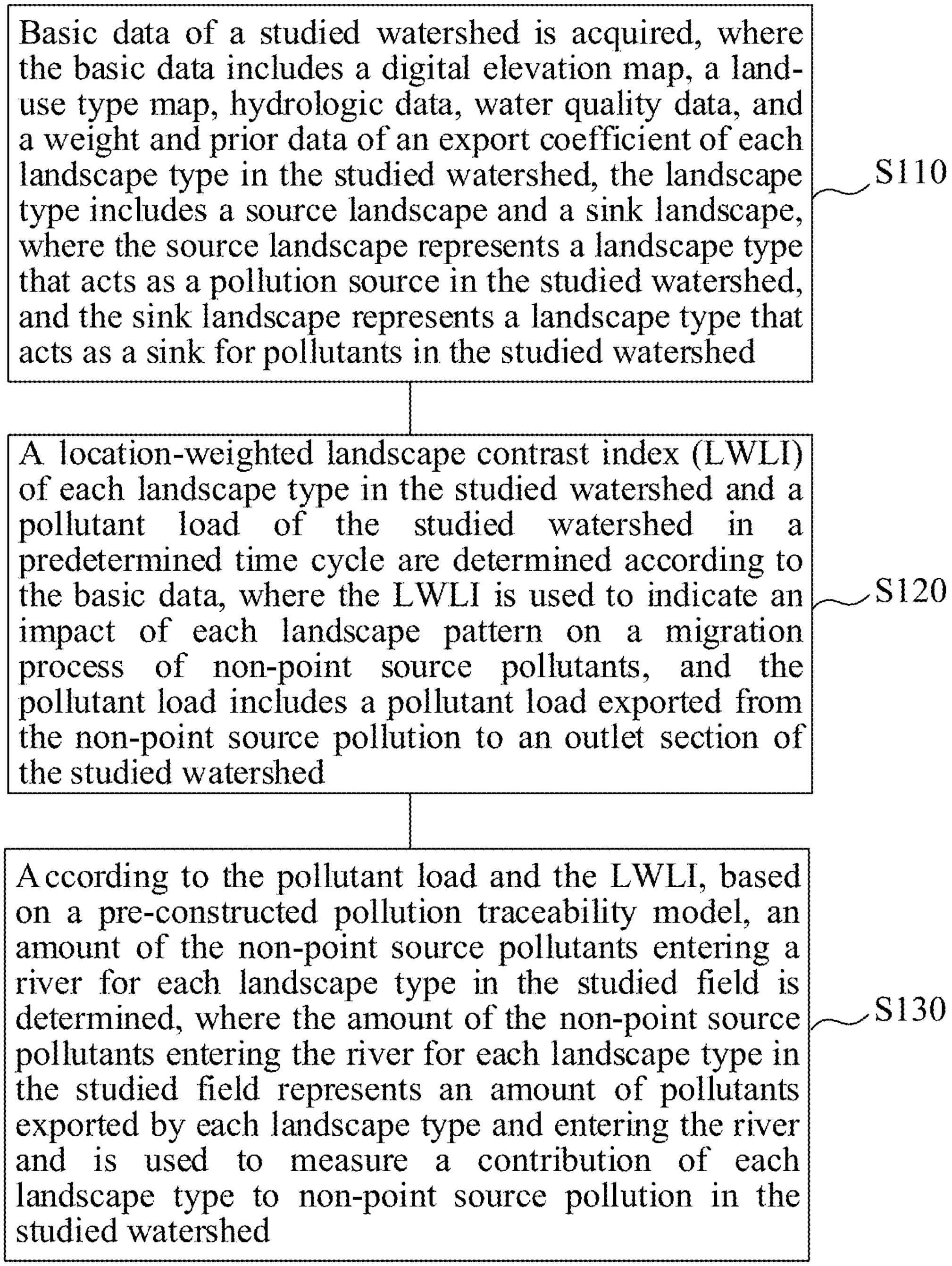
FIG. 1 is a flowchart of a method for traceability of non-point source pollution in a studied watershed according to some embodiments of the present disclosure.

The present disclosure is further described in detail below with reference to the accompanying drawings and embodiments. It can be understood that the specific embodiments described herein are merely intended to explain the present disclosure, rather than to limit the present disclosure. In addition, it should also be noted that, for ease of description, only parts related to the present disclosure are shown in the accompanying drawings.

It should be noted that embodiments in the present disclosure or features in the embodiments may be combined with one another without conflict. The present disclosure will be described in detail below with reference to the accompanying drawings and the embodiments.

It can be understood that with the development of pollution analysis technology and the control of point sources, non-point source pollution is a main pollution source that affects the water environment at present. At present, although a series of control measures, including source control, process interception, terminal treatment, and the like, have been taken, which costs a lot, a non-point source pollution control goal has not been achieved.

It can be understood that a migration process of pollutants from sources to a river is mainly affected by a landscape pattern. That is, for analysis of non-point source pollution in a watershed, the landscape pattern included is a key factor affecting generation, migration and transformation of non-point source pollution. That is, regulating and optimizing the landscape pattern in the watershed can make nutrient elements reach a spatial balance before entering a water body, which is used as a more economical and effective non-point source pollution control strategy. Therefore, it is of great practical significance and application value for watershed landscape optimization design and water quality protection to establish a non-point source pollution traceability model based on landscape patterns and the non-point source pollution process, quantitatively identify key "source" regions of non-point source pollution in the watershed, and solve the core issue of "regulation priority" in landscape pattern optimization.

It can also be understood that there are denitrification, absorption and deposition of aquatic organisms, and other effects during migration of pollutants entering the river from upstream to a watershed outlet, which are calculated by an exponential function that multiplies a migration time by a loss coefficient.

That is, in the embodiments of the present disclosure, in order to improve precise analysis and precise control of non-point source pollution traceability, with reference to each landscape pattern in the watershed, that is, by means of quantitative description of an LWLI, a non-point source pollution traceability model in the watershed is constructed, and an impact of distances between different land-use types of landscapes and receiving water body, a relative elevation, a slope, and the like on a non-point source pollution load in the watershed is considered, so that reverse derivation is performed by using the pollution traceability model that includes the LWLI, so as to accurately analyze non-point source pollution caused by various landscape patterns in the watershed.

In order to better understand a method for inverse traceability of non-point source pollution according to an embodiment of the present disclosure, the method is described below by means of accompanying drawings.

FIG. 1 is a flowchart of a method for inverse traceability of non-point source pollution in a watershed according to an embodiment of the present disclosure. As shown in FIG. 1, the method specifically includes the following steps.

In S110: basic data of a studied watershed is acquired, where the basic data includes a digital elevation map, a land-use type map, hydrologic data, water quality data, and a weight and prior data of an export coefficient of each landscape type in the studied watershed, the landscape type includes a source landscape and a sink landscape, where the source landscape represents a landscape type that acts as a pollution source in the studied watershed, and the sink landscape represents a landscape type that acts as a sink for pollutants in the studied watershed.

In S120: a location-weighted landscape contrast index (LWLI) of each landscape type in the studied watershed and a pollutant load of the studied watershed in a predetermined time cycle are determined according to the basic data, where the LWLI is used to indicate an impact of each landscape pattern on a migration process of non-point source pollutants, and the pollutant load includes a pollutant load exported from the non-point source pollution to an outlet section of the studied watershed.

In S130: according to the pollutant load and the LWLI, based on a pre-constructed pollution traceability model, an amount of the non-point source pollutants entering a river for each landscape type in the studied field is determined, where the amount of the non-point source pollutants entering the river for each landscape type in the studied field represents an amount of pollutants exported by each landscape type and entering the river and is used to measure a contribution of each landscape type to non-point source pollution in the studied watershed.

Specifically, in the embodiment of the present disclosure, for the method for traceability of non-point source pollution in the studied watershed, the basic data in the studied watershed may be acquired first.

The basic data includes the digital elevation map, land-use types, the hydrologic data, the water quality data, and the prior data of the export coefficient and the weight of each landscape type in the studied watershed. The landscape type includes the source landscape and the sink landscape, where the source landscape refers to a landscape type that acts as "a pollution source" in the watershed, such as residential land and dry land, and the sink landscape refers to "a sink" of crop pollutants corresponding to some landscape types in the watershed, such as woodland and grassland.

Figure 2:
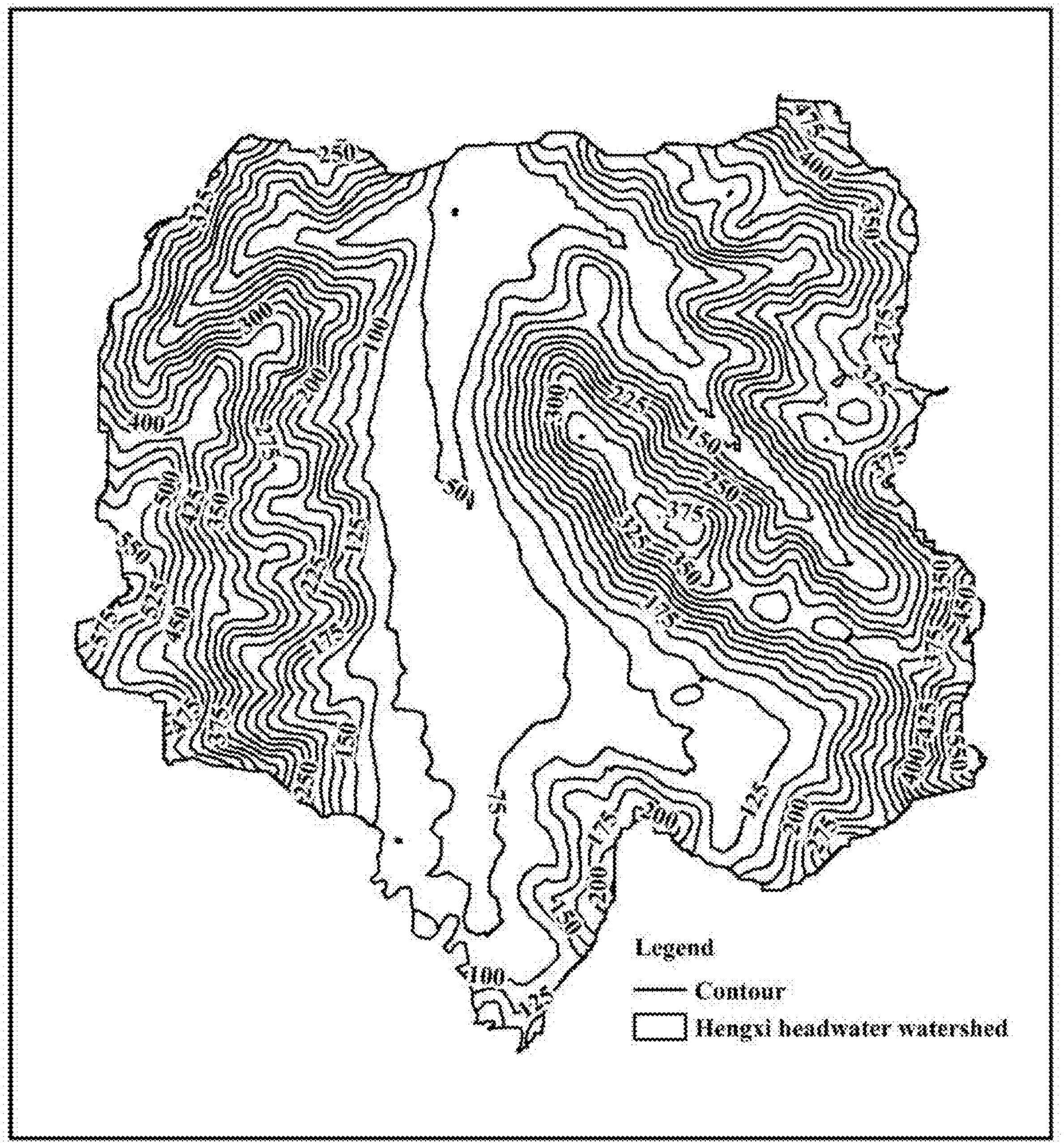
FIG. 2 is a schematic diagram of a digital elevation of a headwater watershed of Hengxi Reservoir.
Figure 3:
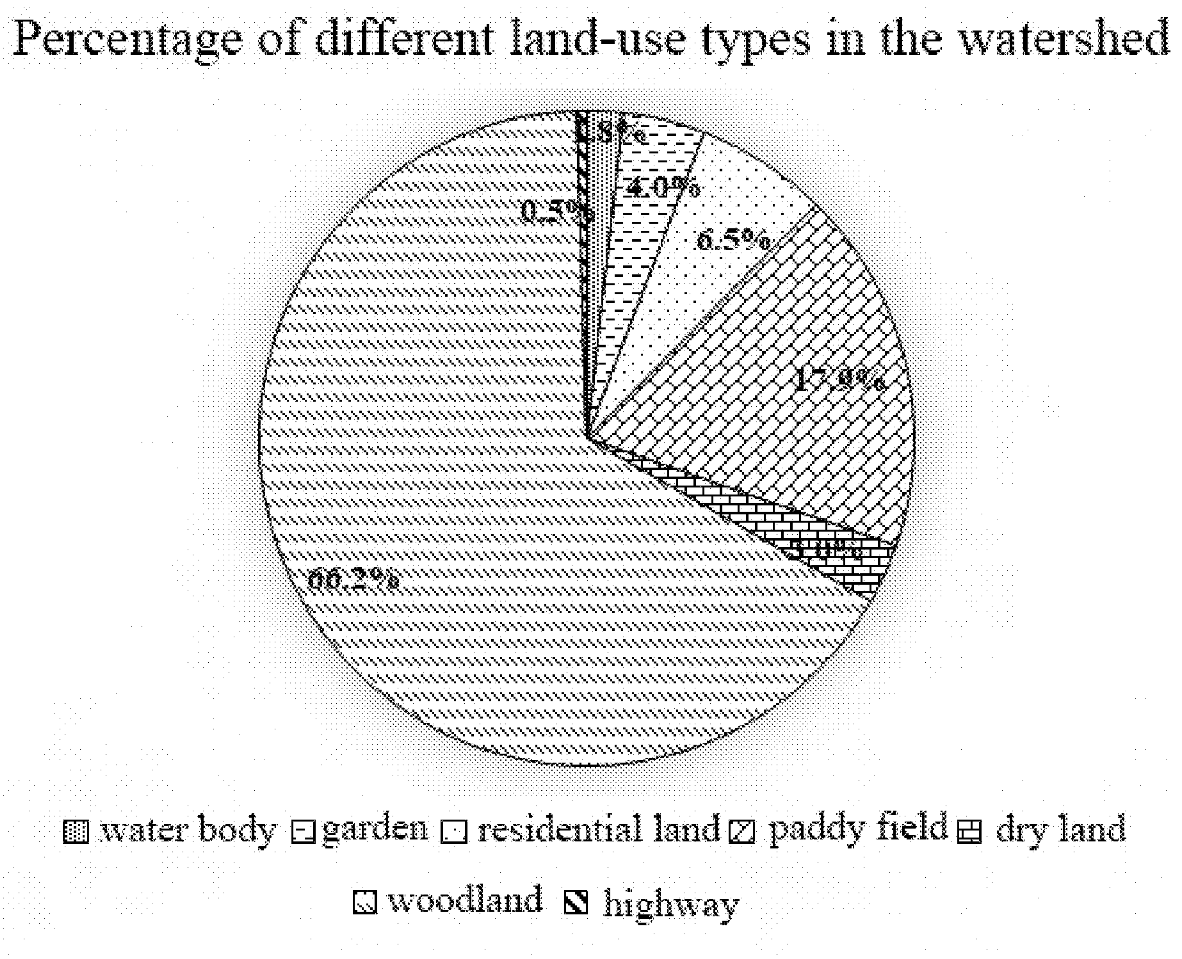
FIG. 3 is a schematic diagram of land-use types in the headwater watershed of Hengxi Reservoir.

For example, with an example in which a headwater watershed of Hengxi Reservoir shown in FIG. 2 as a studied watershed, a digital elevation map in the studied watershed and a land-use type map shown in FIG. 3 can be obtained.

The sink landscape may include water body, woodland, paddy field, dry land, highway, residential land and garden as a source landscape. That is, land-use type in the studied watershed may be divided into a source landscape and a sink landscape.

Correspondingly, the prior data may include a corresponding export coefficient and a weight of each landscape type/land-use type.

Figure 4:
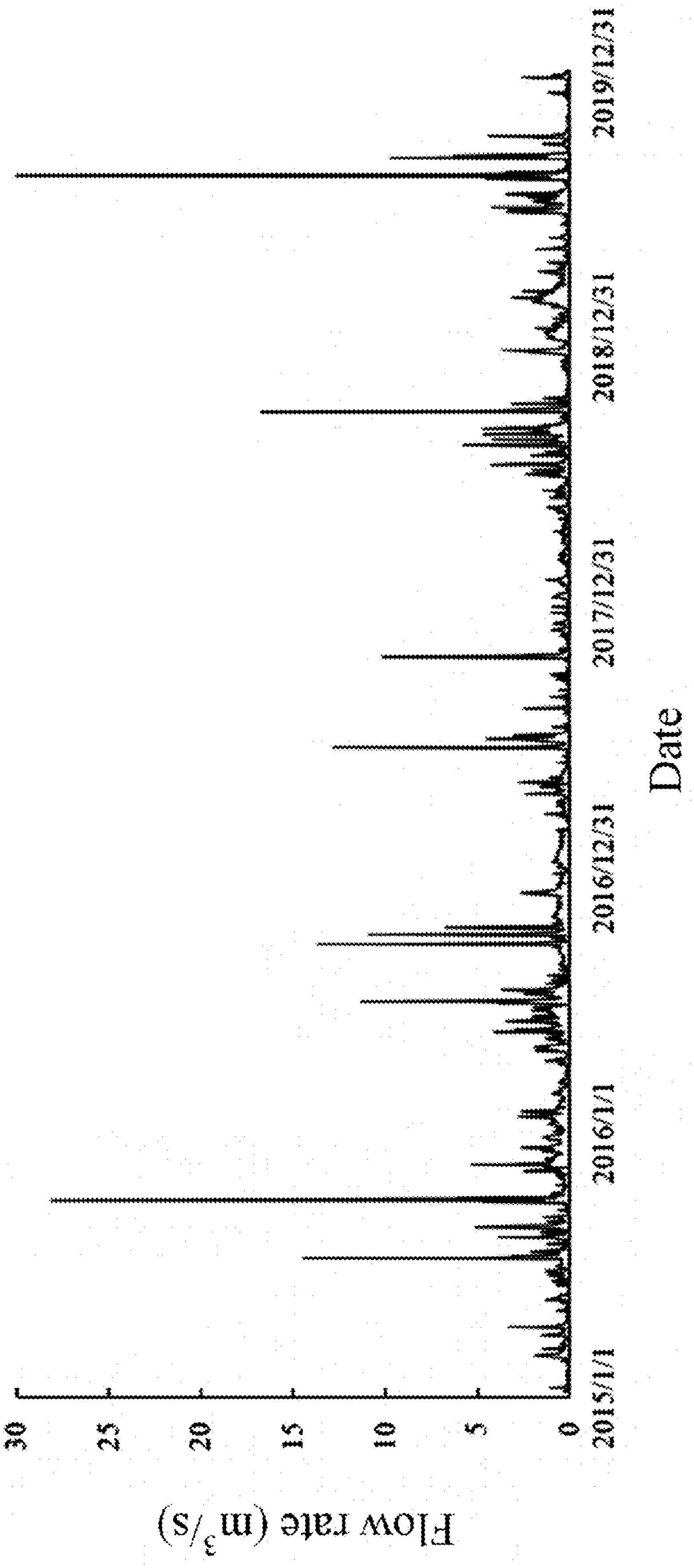
FIG. 4 is a schematic diagram of a daily flow at an outlet section of the headwater watershed of Hengxi Reservoir.

The hydrologic data and the water quality data may be measured in a predetermined time cycle. For example, water quality data in the studied watershed monitored regularly every month, including TN concentration data, and a daily flow rate at the outlet section monitored daily are used as the hydrologic data, as shown in FIG. 4.

The prior data of the landscape type may include prior distribution of an export coefficient corresponding to each landscape.

Specifically, prior information of export coefficient values of pollutants corresponding to different landscape types may be collected by consulting literature, and prior distribution of a corresponding export coefficient of each landscape type is calculated.

That is, the landscape type may be divided into a "source landscape" and a "sink landscape" according to an impact of each land-use type on the non-point source pollution process in the watershed, and a weight of each landscape type may be determined.

For example, the land-use types in the studied watershed may be divided into seven types, in which water body and woodland are the "sink landscape", and paddy field, dry land, highway, residential land and garden are the "source landscape".

For example, various "source landscapes" and "sink landscapes" in the headwater watershed of Hengxi Reservoir are taken as examples for explanation. In this watershed, since water body and highway have an area less than 3% area of the watershed, the water body and the highway may be ignored in the subsequent study.

By consulting relevant literature, prior distribution of export coefficients and weights of various "source and sink" landscapes in the headwater watershed of Hengxi Reservoir are calculated by means of collected export coefficient values, as shown in Table 1.

TABLE 1

Prior distribution of export coefficients and weights of "source and sink" landscapes in the headwater watershed of Hengxi Reservoir

| Land-use | Sink landscape Woodland | Source landscape Paddy field | Dry land | Garden | Residential land |
|---|---|---|---|---|---|
| Prior distribution of export coefficients | N (8.68, 1.64) | N (20.3, 5.92) | N (64.75, 6.13) | N (34.16, 3.34) | N (42.96, 7.0) |
| Weight | 1.00 | 0.31 | 1.00 | 0.52 | 0.66 |

Further, after the aforementioned basic data is acquired, a pollutant load of the studied watershed in a predetermined time period and an LWLI of each landscape in the studied field may be determined according to the basic data, where the LWLI is used to indicate an impact of each landscape pattern on a migration process of pollutants, and the pollutant load includes a pollutant load exported from a non-point source to the outlet section of the watershed.

Further, after the pollutant load of the studied watershed in the predetermined time period and each LWLI in the studied field are determined by means of the aforementioned step, an amount of non-point source pollutants entering the river for each landscape type in the studied field may be determined according to the pre-constructed pollution traceability model in the studied watershed, where the amount of non-point source pollutants entering the river for each landscape type in the studied field indicates a contribution of a corresponding landscape type to non-point source pollution in the watershed.

That is, the parameters determined above may be substituted into the pre-constructed model to determine the parameters in the model by means of an inversion method. That is, the parameters in the model are calibrated and verified to obtain parameter values to be solved. Finally, according to the determined parameters, the amount of non-point source pollutants entering the river for each landscape type in the studied field is determined, and finally the impact of each landscape pattern in the studied watershed on non-point source pollution is determined.

It may be understood that in the method for traceability of non-point source pollution in a watershed according to the embodiment of the present disclosure, during the process of tracing non-point source pollution in the studied watershed, the basic data in the studied watershed is acquired first, then the LWLI of each landscape type in the studied watershed and a pollutant load of the studied watershed in the predetermined time cycle are determined by means of the acquired basic data, and then according to the determined LWLI and pollutant load, an amount of pollutants entering the river, which represents a contribution of each landscape type to non-point source pollution in the studied watershed, is solved based on the pre-constructed pollution traceability model. That is, in the present disclosure, the determined LWLI included in the pollution traceability model can show an impact of each landscape pattern on a migration process of non-point source pollutants, and thus determined parameters are used to solve parameters in the pollution traceability model, which is conductive to accurately obtain parsing results of non-point source pollution sources in the watershed, quantitatively evaluate an amount of non-point source pollutants entering the river for different landscape types in the watershed, and effectively identify key pollution sources of non-point source pollution in the watershed, thereby providing effective guidance for control of non-point source pollution in the watershed, and having the characteristics of easy data acquisition and higher accuracy of obtained results, and the like. Therefore, the failure to fully consider the impact of a watershed landscape spatial structure on the non-point source pollution process in related technologies is avoided, and quantitative traceability of non-point source pollution in the watershed is achieved.

In some embodiments, in some embodiments of the present disclosure, the LWLI includes a relative distance-based LWLI, a relative elevation-based LWLI and a slope-based LWLI. An LWLI of each landscape in the studied watershed is determined according to the basic data. Specifically, the relative distance-based LWLI, the relative elevation-based LWLI and the slope-based LWLI may be calculated according to the basic data, and then the calculated relative distance-based LWLI, relative elevation-based LWLI and slope-based LWLI are fused to obtain the LWLI.

Figure 5:
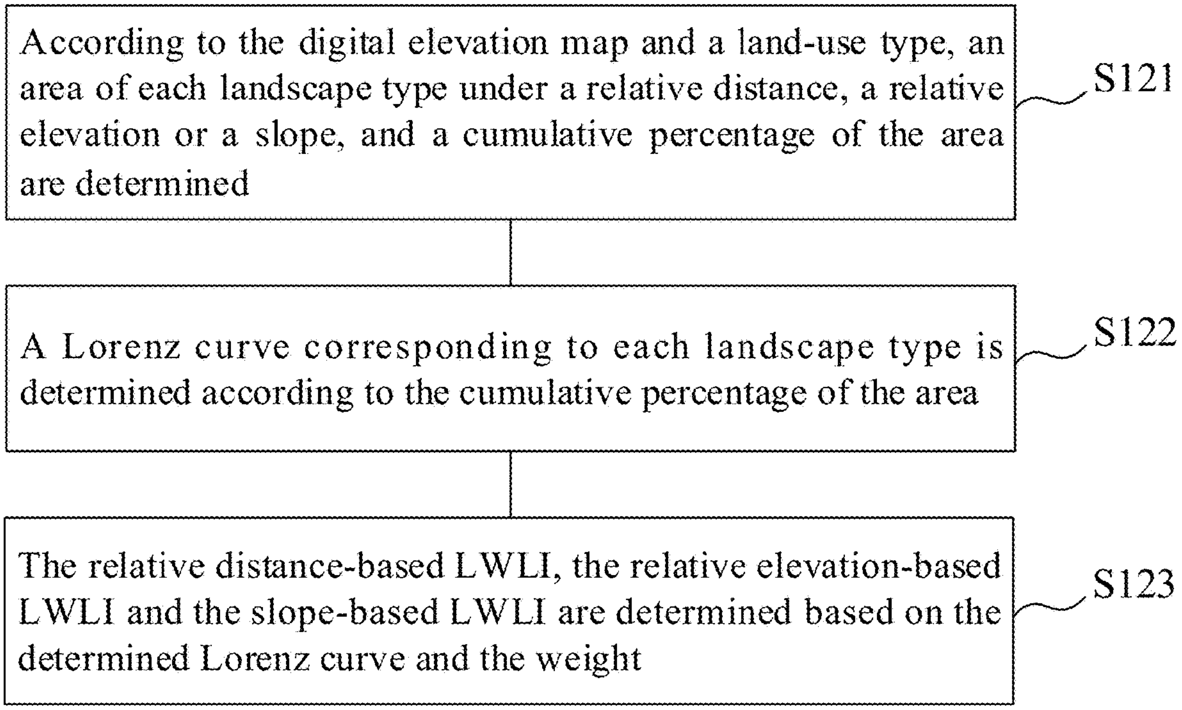
FIG. 5 is a flowchart of a method for inverse traceability of non-point source pollution in a studied watershed according to some embodiments of the present disclosure.

Specifically, in some embodiments, the calculation of each LWLI, as shown in FIG. 5, may specifically include the following steps.

In S121: according to the digital elevation map and a land-use type, an area of each landscape type under a relative distance, a relative elevation or a slope, and a cumulative percentage of the area are determined.

In S122: a Lorenz curve corresponding to each landscape type is determined according to the cumulative percentage of the area.

In S123: the relative distance-based LWLI, the relative elevation-based LWLI and the slope-based LWLI are determined based on the determined Lorenz curve and the weight.

Specifically, after the aforementioned basic data is acquired, the area of a land-use type corresponding to each landscape pattern under the relative distance, the relative elevation or the slope and the cumulative percentage of the area may be first determined according to digital elevation image data in the basic data and each landscape pattern in land-use types in the studied watershed, and then the Lorenz curve may be drawn with the cumulative percentage of the relative distance (the relative elevation or the slope) as an abscissa axis and the cumulative area of each of different types of source and sink landscapes under the corresponding horizontal coordinates as a vertical coordinate. Finally, each LWLI is calculated by using the drawn Lorenz curve and the weight of each land-use type corresponding to each landscape pattern in the aforementioned basic data.

A specific formula is as follows:

$$LWLI_{Relative\ distance/relative\ elevation/slope} = \frac{\sum_{i=1}^{m} A_{Sourcei} \times w_i \times AP_i}{\sum_{j=1}^{n} A_{Sinkj} \times w_j \times AP_j},$$

where m represents a total number of source landscapes in the studied watershed; n represents a total number of sink landscapes in the studied watershed; $A_{Source\ i}$ and $A_{Sink\ i}$ represent areas enclosed by Lorenz curves of an $i^{th}$ source landscape and a $j^{th}$ sink landscape in the studied watershed, respectively, and $AP_i$ and $AP_j$ represent area percentages of the $i^{th}$ source landscape and the $j^{th}$ sink landscape in the watershed, respectively; and $w_i$ and $w_j$ represent weights of the $i^{th}$ source landscape and the $j^{th}$ sink landscape, respectively.

It can be understood that the Lorenz curve drawn in the embodiment of the present disclosure is obtained by calculating areas of an $i^{th}$ "source" landscape and a $j^{th}$ "sink" landscape in different distance ranges with a distance (elevation or slope) relative to the watershed outlet as a horizontal coordinate and an interval of u meters, and drawing with a corresponding cumulative area thereof as a vertical coordinate. Areas enclosed by "source" and "sink" Lorenz curves are calculated by means of MATLAB.

For example, for the various "source and sink" landscapes in the headwater watershed of Hengxi Reservoir, a calculation process of each corresponding LWLI is as follows.

Figure 6:
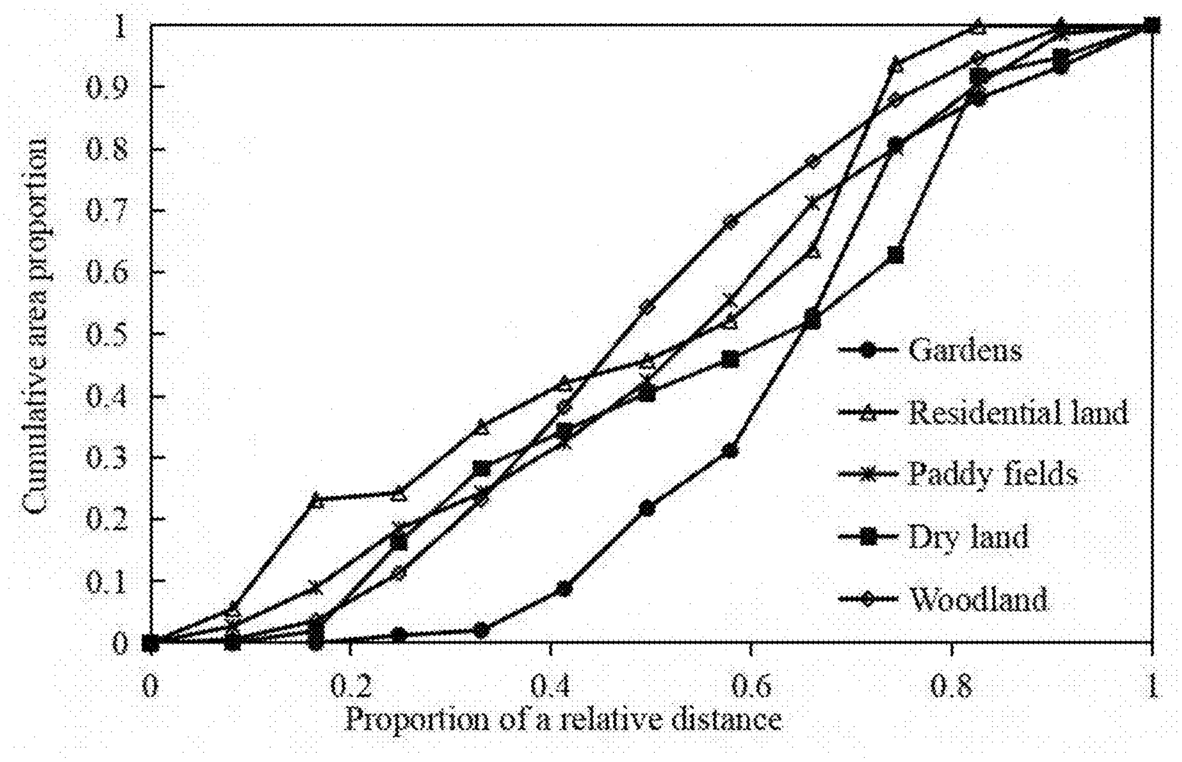
FIG. 6 is a schematic diagram of a Lorenz curve corresponding to a relative distance of each land-use type.

For example, for the relative distance-based LWLI, areas of various "source landscapes" and "sink landscapes" in different relative distance ranges are first calculated with the watershed outlet as a circle center and 500 meters as a radius interval. A Lorenz curve is drawn with the relative distance as a horizontal coordinate, and a cumulative area proportion of each of "source landscapes" and "sink landscapes" as a vertical coordinate, as shown in FIG. 6.

The relative distance-based LWLI is calculated by using the following formula:

$$LWLI_{Relative\ distance} = \frac{\sum_{i=1}^{m} A_{Sourcei} \times w_i \times AP_i}{\sum_{j=1}^{n} A_{Sinkj} \times w_j \times AP_j}$$

where $A_{Source\ i}$ and $A_{Sink\ i}$ represent areas enclosed by Lorenz curves of an $i^{th}$ source landscape and a $j^{th}$ sink landscape in the studied watershed, respectively, and $AP_i$ and $AP_j$ represent area percentages of the $i^{th}$ source landscape and the $j^{th}$ sink landscape in the watershed, respectively; and $w_i$ and $w_j$ represent weights of the $i^{th}$ source landscape and the $j^{th}$ sink landscape, respectively.

As shown in Table 1, a calculation result thereof was 0.21.

Figure 7:
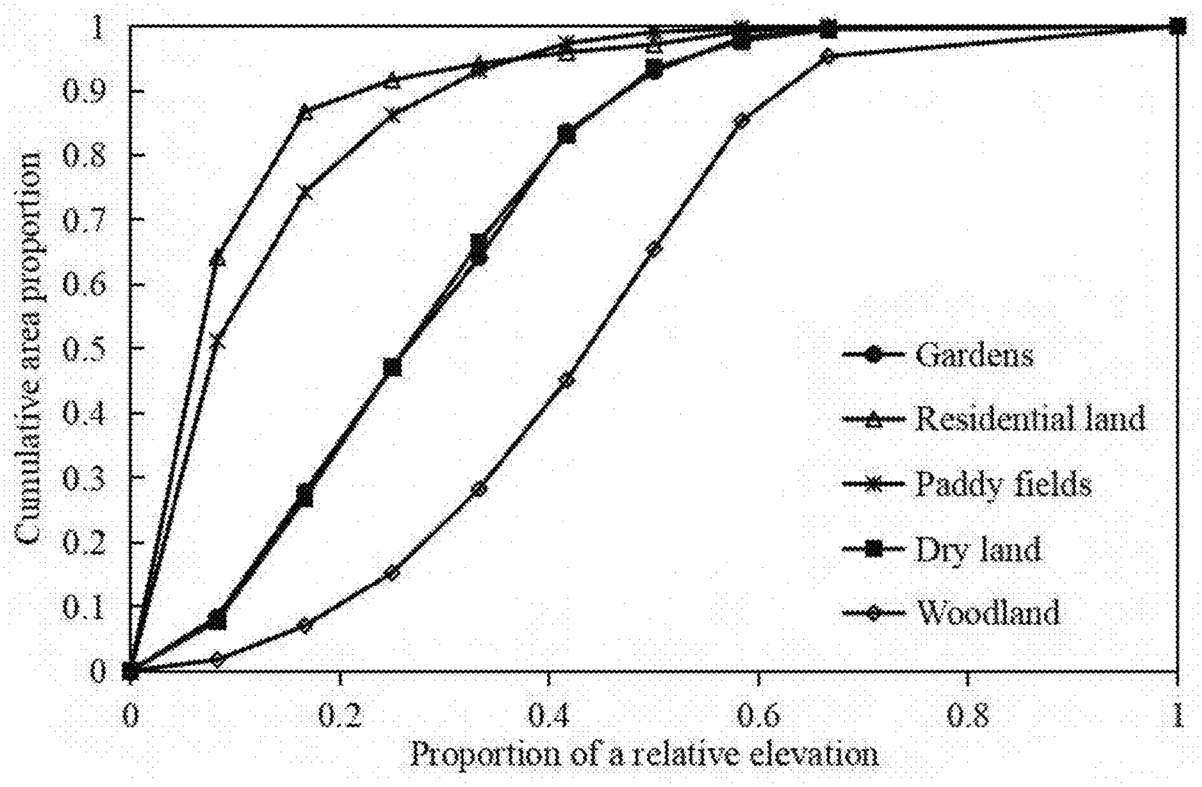
FIG. 7 is a schematic diagram of a Lorenz curve corresponding to a relative elevation of each land-use type.

For another example, for the relative elevation-based LWLI, the relative elevation-based LWLI is calculated. The relative elevation of each place in the watershed relative to the watershed outlet is calculated by using the digital elevation map, and then areas of various "source landscapes" and "sink landscapes" in different relative elevation ranges are calculated at intervals of 50 meters. A Lorenz curve is drawn with the relative elevation as a horizontal coordinate, and a cumulative area of each of "source landscapes" and "sink landscapes" as a vertical coordinate, as shown in FIG. 7.

The relative elevation-based LWLI is calculated by using the following formula:

$$LWLI_{Relative\ elevation} = \frac{\sum_{i=1}^{m} A_{Sourcei} \times w_i \times AP_i}{\sum_{j=1}^{n} A_{Sinkj} \times w_j \times AP_j}$$

where $A_{Source\ i}$ and $A_{Sink\ i}$ represent areas enclosed by Lorenz curves of an $i^{th}$ source landscape and a $j^{th}$ sink landscape in the studied watershed, respectively, and $AP_i$ and $AP_j$ represent area percentages of the $i^{th}$ source landscape and the $j^{th}$ sink landscape in the watershed, respectively; and $w_i$ and $w_j$ represent weights of the $i^{th}$ source landscape and the $j^{th}$ sink landscape, respectively.

As shown in Table 1, a calculation result thereof was 0.32.

Figure 8:
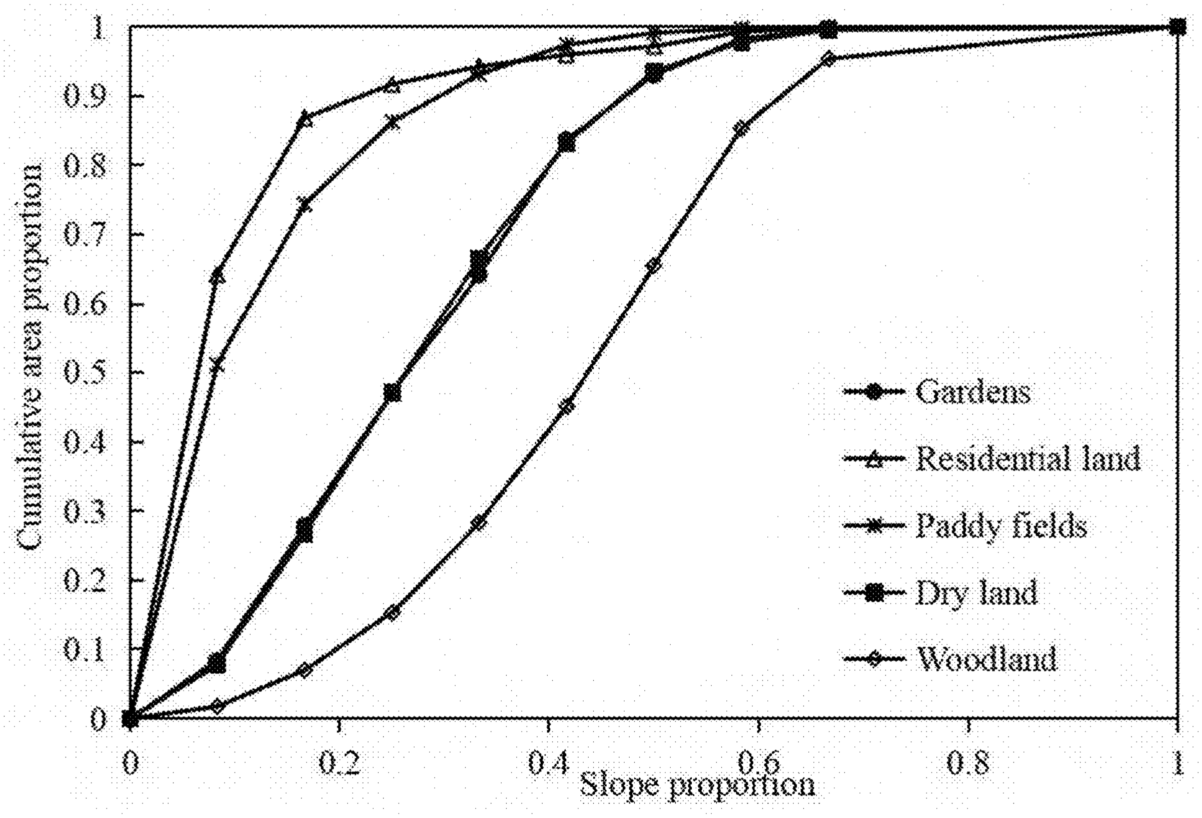
FIG. 8 is a schematic diagram of a Lorenz curve corresponding to a slope of each land-use type.

For another example, for the slope-based LWLI, the slope-based LWLI is calculated. A slope grid in the watershed is calculated by using the digital elevation map. Areas of various "source landscapes" and "sink landscapes" in different slope ranges are calculated at intervals of 4°. A Lorenz curve is drawn with the slope as a horizontal coordinate, and a cumulative area proportion of each of "source landscapes" and "sink landscapes" as a vertical coordinate, as shown in FIG. 8. The slope-based LWLI is calculated by using the following formula:

$$LWLI_{Slope} = \frac{\sum_{i=1}^{m} A_{Sourcei} \times w_i \times AP_i}{\sum_{j=1}^{n} A_{Sinkj} \times w_j \times AP_j}$$

where $A_{Source\ i}$ and $A_{Sink\ i}$ represent areas enclosed by Lorenz curves of an $i^{th}$ source landscape and a $j^{th}$ sink landscape in the studied watershed, respectively, and $AP_i$ and AP; represent area percentages of the $i^{th}$ source landscape and the $j^{th}$ sink landscape in the watershed, respectively; and $w_i$ and $w_j$ represent weights of the $i^{th}$ source landscape and the $j^{th}$ sink landscape, respectively.

As shown in Table 1, a calculation result thereof was 0.34.

Further, after the relative distance-based LWLI, the relative elevation-based LWLI and the slope-based LWLI are determined by means of the aforementioned method, the calculated relative distance-based LWLI, relative elevation-based LWLI and slope-based LWLI can be fused.

It can be understood that the location-weighted landscape contrast index (LWLI) which comprehensively considers an impact of the relative distance, the relative elevation and the slope on the non-point source pollution process is calculated. Larger values of the relative distance-based LWLI ($LWLI_{Relative\ distance}$) and the relative elevation-based LWLI ($LWLI_{Relative\ elevation}$) indicate a relatively greater nutrient loss at the watershed outlet, while the slope-based LWLI ($LWLI_{Slope}$) indicates the opposite case.

In some embodiments of the present disclosure, the values calculated in the aforementioned steps may be substituted into the following formula to calculate a comprehensive LWLI of non-point source pollution in the watershed:

$$LWLI = LWLI_{Relative\ distance} \times LWLI_{Relative\ elevation} / LWLI_{Slope}.$$

In some embodiments, in some embodiments of the present disclosure, after the basic data is acquired, the pollutant load of the studied watershed in the predetermined time period may be calculated by means of a LOADEST model.

Specifically, after the basic data is collected, the pollutant load in a predetermined time cycle in the predetermined time period may be determined by using the hydrologic data and the water quality data in the collected basic data.

Figure 9:
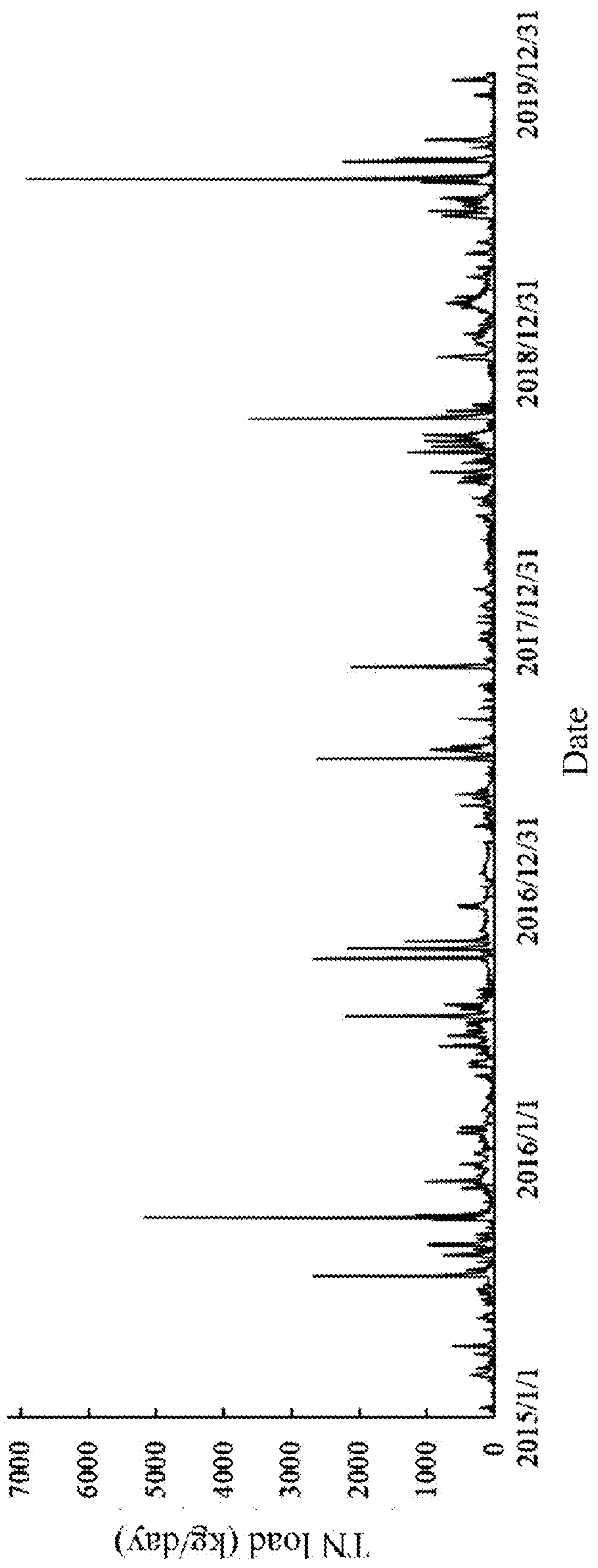
FIG. 9 is a schematic diagram of a daily load at a watershed outlet.

For example, for the headwater watershed of Hengxi Reservoir, the LOADEST model can be used to calculate a daily load at the watershed outlet based on a monthly monitored discrete TN concentration and flow data, as shown in FIG. 9.

Figure 10:
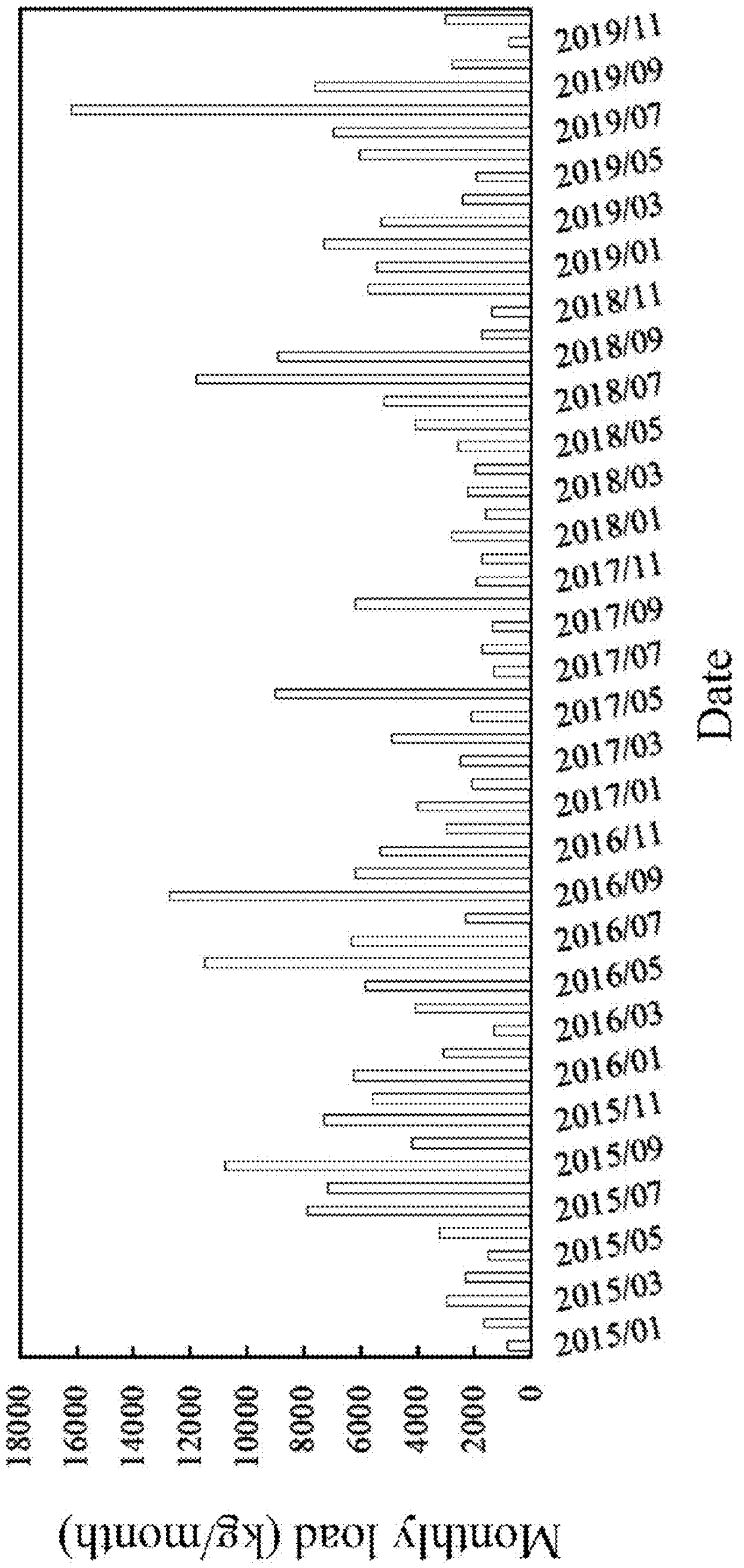
FIG. 10 is a schematic diagram of a monthly load at the watershed outlet.
Figure 11:
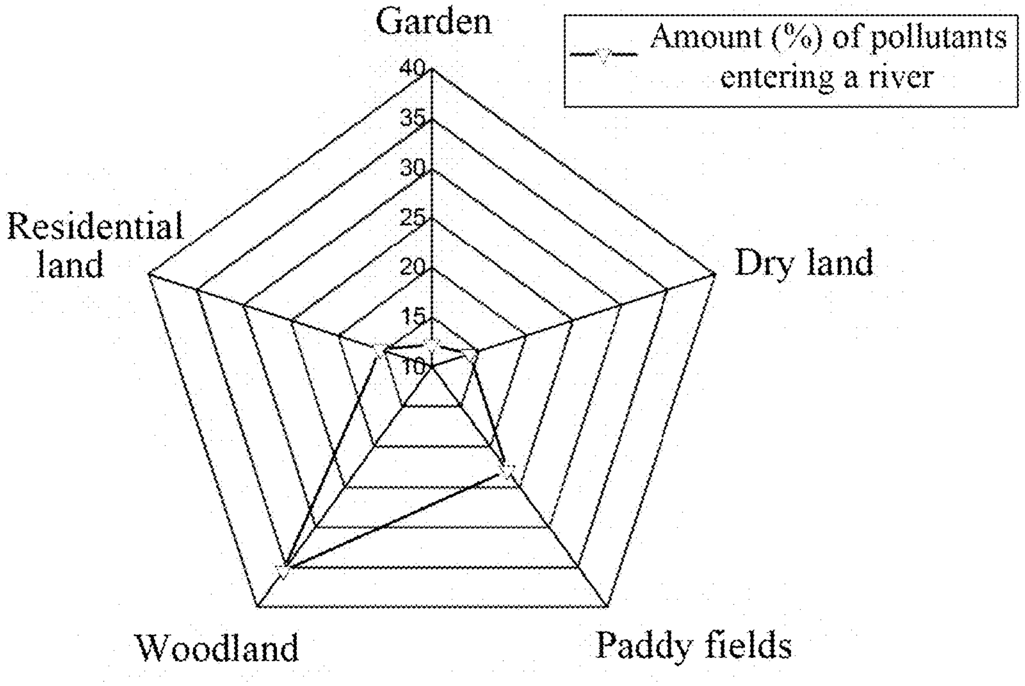
FIG. 11 is a schematic diagram of a percentage of total nitrogen (TN) entering a river for each land-use type according to an embodiment of the present disclosure.

Further, according to the daily load at the watershed outlet, monthly TN load from year 2015 to year 2019 are calculated, as shown in FIG. 10.

It can be understood that for the calculation of a non-point source pollution input quantity, the process of non-point source pollutants in a watershed from a source to the watershed outlet may be divided into the following: export of a pollution source (source)—a migration process of pollutants from the source to the river (flow)—entry of the pollutants into a water body (sink)—migration from the water body to the watershed outlet (point). An export quantity (discharge quantity) of pollutants is accounted by using an improved export coefficient model. Different land-use types have different runoff flow rates in a certain rainfall event. Due to the lack of data of surface runoff flow rates of various land-use types, and in view of the fact that the runoff flow rates generated by different land-use types in a certain time period have a consistent change trend with time, in this study, it is assumed that a monthly variability of each land-use export coefficient in the watershed is described by means of a change in ratio of a monthly surface runoff flow rate to a multi-year average surface runoff flow rate over time. The migration process of pollutants from the source to the river is mainly affected by a landscape pattern, which is described quantitatively by using the LWLI. There are denitrification, absorption and deposition of aquatic organisms, and other effects during migration of pollutants entering the river from upstream to a watershed outlet, which are calculated by an exponential function that multiplies a migration time by a loss coefficient. Therefore, a non-point source pollutant calculation formula coupling a pollution source export quantity calculation module, a module for calculating an impact of landscape patterns on a migration process of non-point source pollution, a river purification quantity calculation module, and other modules is as follows:

That is, in some embodiments of the present disclosure, the constructed traceability model may be specifically expressed as follows:

$$NS_g = \sum_{\eta=1}^{m+n} \left( \frac{f(Q_g)}{f(\overline{Q})} \right) e^{\eta} A_{\eta} LWLI \exp\left(-k \frac{T_g}{2}\right),$$

where $NS_g$ represents a pollutant load exported from a non-point source to the outlet section of the studied watershed in a $g^{th}$ time cycle; η represents a number of land-use types, with a total of m+n; $\overline{Q}$ represents an average runoff flow rate in a predetermined time cycle; $Q_g$ represents a runoff flow rate in the $g^{th}$ time cycle; $f(\ )$ represents a functional relationship between a runoff flow rate at an outlet of the studied watershed and a pollutant load in runoff; $e^{\eta}$ represents a pollutant export coefficient of a $\eta^{th}$ land-use type; $A_\eta$ represents an area of the $\eta^{th}$ land-use type; a subscript g represents a $g^{th}$ time cycle; and k represents a first-order kinetic loss rate constant of river pollutants.

For example, when the aforementioned predetermined time cycle is a month, $NS_g$ represents a pollutant load exported from a non-point source to the outlet section of the studied watershed in the $g^{th}$ month; and $Q_g$ represents a runoff flow rate in the $g^{th}$ month.

It can be understood that for the parameters in the aforementioned constructed traceability model, land-use types in the watershed are divided into $f$ types. Therefore, the above formula contains 5+η+2h (h is a number of point sources) observed variables ($L_g$, $f(Q_g)$, $f(\overline{Q})$, $A_\eta$, LWLI, $T_g$, $$L_g^h$$

and $$T_g^h$$

and η+1 non-measured parameters ($e^\eta$ and k), and the non-measured parameters can be solved by means of a Bayesian method through using WinBUGS software.

The non-measured parameters can represent a contribution of landscape patterns to non-point source pollution in the whole watershed. That is, the known parameters determined above are substituted into the aforementioned constructed model, a parameter to be solved is determined by using a predetermined algorithm, and finally an impact of each landscape pattern in the watershed on non-point source pollution can be determined.

In some embodiments, the determining, according to the pollutant load and the LWLI of each landscape, based on a pre-constructed pollution traceability model, an amount of non-point source pollutants entering the river for each landscape type in the studied field specifically includes the following steps.

In S131: according to the pollutant load and the LWLI and based on the pre-constructed pollution traceability model, parameter to be determined in the pollution traceability model is determined by using a Bayesian inversion algorithm, where the parameter to be determined includes a pollutant export coefficient corresponding to each land-use type and a first-order kinetic loss rate constant of river pollutants.

In S132: an amount of non-point source pollutants entering the river for each land-use type in the studied field is determined according to the pollutant export coefficient corresponding to each land-use type.

Specifically, the pollutant load, the LWLI of each landscape, the prior distribution of the export coefficient of each landscape type and a runoff correction coefficient determined in the aforementioned embodiments are input into the constructed traceability model, and then solving is performed by means of the Bayesian method. For example, the aforementioned solving can be achieved by means of WinBUGS software.

The parameter to be determined, that is, a pollutant export coefficient value ($kg \cdot ha^{-1} \cdot month^{-1}$) for each land-use type, can be obtained.

In some embodiments, the parameter to be determined may further include the first-order kinetic loss rate constant ($d^{-1}$) of river pollutants, and the first-order kinetic loss rate constant ($d^{-1}$) of river pollutants can reflect a self-purification ability of a water body.

Finally, an amount of non-point source pollutants entering the river for each land-use type in the studied field can be determined by using the determined solved parameter. For example, a product of a pollutant export coefficient corresponding to each land-use type and the area thereof, the LWLI and the runoff correction coefficient may be used as the amount of pollutants entering the river, so as to reflect a contribution of a corresponding landscape type to non-point source pollution in the watershed.

In some embodiments, in some embodiments of the present disclosure, in order to improve traceability accuracy, the aforementioned parameter to be solved can be verified after being obtained.

Specifically, a part of the observed data may be used to calibrate the model to obtain each parameter value to be solved; and then the solved parameters are substituted into the model and verified by means of another part of the data. A determining coefficient ($R^2$) and a Nash-Sutcliffe efficiency coefficient (NSE) are used to evaluate a fitting effect between simulation results and observed values, so as to evaluate the applicability of the model in this studied area. Formulas for calculating R2 and the NSE are respectively as follows:

$$R^2 = \left( \frac{\sum_{i=1}^{n} (x_i - \overline{x})(y_i - \overline{y})}{\sqrt{\sum_{i=1}^{n} (x_i - \overline{x})^2} \sqrt{\sum_{i=1}^{n} (y_i - \overline{y})^2}} \right)^2; \text{ and}$$

$$NSE = 1 - \frac{\sum_{i=1}^{n} (y_i - x_i)^2}{\sum_{i=1}^{n} (y_i - \overline{y})^2},$$

where n represents a number of data; $x_i$ and $y_i$ represent an $i^{th}$ simulated value and observed value, respectively; and $\overline{x}$ and $\overline{y}$ represent average values of simulated values and observed values, respectively.

A larger $R^2$ value indicates a better simulation result, and a simulated value closer to a measured value. A larger NSE indicates higher efficiency and better adaptability of the model. Generally, when NSE>0.8, a simulation result of the model may be regarded as being quite accurate, and when NSE>0.5, a simulation result of the model may be regarded as meeting accuracy requirements.

Figure 12:
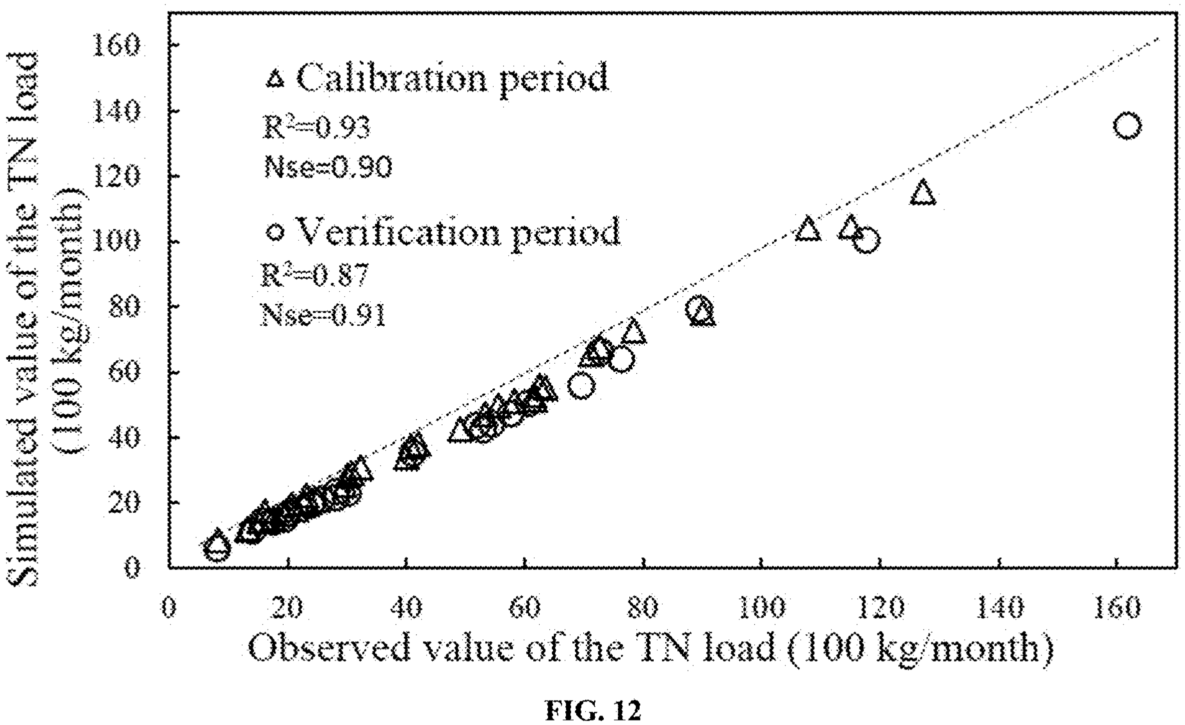
FIG. 12 is a schematic diagram showing results of a calibration period and a verification period of a pollution traceability model according to an embodiment of the present disclosure.

For example, for the above example, that is, in the headwater watershed of Hengxi Reservoir, the model is constructed by means of the method provided in the above embodiment, and after the parameter to be solved is solved by the inversion algorithm, when verification is performed by using the above formula, results of the model in a calibration period and a verification period are shown in FIG. 12.

In addition, it can also be understood that in some cases, the pollutant load in the studied watershed may include point source pollution, upstream water body pollution and tributary pollution in addition to the non-point source pollution. Correspondingly, when the pollutant load is constructed, a one-dimensional river water quality equation may be used to describe the pollution of the river in this watershed. The pollutant load at the river outlet section is composed of pollutants input from an upstream inlet section, pollutants input from tributaries between the inlet and outlet sections, pollutants input from a non-point source and pollutants input from a point source after degradation by the river. According to the principle of input-export balance of the pollutant load in a river segment, a formula for calculating a pollutant load at the end of the river segment is obtained, that is, the pollutant traceability model may be expressed as follows:

$$L_g = L_g^u \exp(-kT_g) + NS_g + \sum_{h=1}^{h} L_g^h \exp(-kT_g^h),$$

where $L_g$ represents a pollutant load (kg·month$^{-1}$) of the river outlet section in the $g^{th}$ month, which is further calculated by using the daily pollutant load at the watershed outlet estimated by using the LOADSET model;

$$L_g^u$$

represents a pollutant load (kg·month$^{-1}$) input from an upstream water body in the $g^{th}$ month; $NS_g$ represents a pollutant load (kg·month$^{-1}$) exported from a non-point source to the outlet section of the watershed in the $g^{th}$ month;

$$L_g^h$$

represents a pollutant load input from an $h^{th}$ tributary or a point source in the $g^{th}$ month; h represents the $h^{th}$ tributary; and $T_g$ indicates a time (d) required for non-point source pollutants migrated from the head to the end of the segment, and the migration time is obtained by dividing a river length by a water flow velocity. v represents an average water flow velocity, and the flow velocity is a function of flow estimation; and $$T_g^h$$

represents a time (d) required for pollutants input from the $h^{th}$ tributary or the point source to migrate from an inlet point to the end of the river segment.

For example, for the headwater watershed of Hengxi Reservoir mentioned above, export coefficients of different landscape types and a first-order kinetic loss rate value of river pollutants in the watershed are calculated. Based on a non-point source pollution load model of landscape patterns, parameter values to be estimated are obtained by means of the Bayesian method. It can be learned according to preliminary investigation that, enterprises and factories with large sewage discharge in an upper watershed of Hengxi Reservoir have been shut down or relocated, and it is strictly forbidden to build new polluting enterprises or factories in this watershed. Therefore, point sources in this watershed may be ignored. Since the selected Hengxi watershed is a headwater watershed, there are no upstream river segments that are input by pollutants. Therefore, a simplified non-point source pollution load model based on landscape patterns is used to calculate k and river entry coefficients of different landscape types by inverse traceability method. The specific formula is shown in the above formula (1).

That is, $$L_g = \sum_{\eta=1}^{p}\left(\frac{f(Q_g)}{f(\overline{Q})}\right)e^{\eta}A_{\eta}LWLI\exp\left(-k\frac{T_g}{2}\right),$$

where $L_g$ represents a pollutant load (kg·month$^{-1}$) at the river outlet section in the $g^{th}$ month, and η represents a number of land-use types, with a total of m+n; $\overline{Q}$ represents an average runoff flow rate (m$^3$·s$^{-1}$) in a studied time period; $Q_g$ represents a runoff flow rate (m$^3$·s$^{-1}$) in the $g^{th}$ month; $f($ $)$ represents a functional relationship between a runoff flow rate at the watershed outlet and a pollutant load in runoff; $e^{\eta}$ represents a pollutant export coefficient (kg·ha$^{-1}$·month$^{-1}$) of a $\eta^{th}$ land-use type; $A_{\eta}$ represents an area (ha) of the $\eta^{th}$ land-use type; a subscript g represents the $g^{th}$ month; and k represents a first-order kinetic loss rate constant (d$^{-1}$) of river pollutants. $T_g$ represents a time (d) required for non-point source pollutants migrated from the head to the end of the segment, and the migration time is obtained by dividing the river length by the water flow velocity. v represents an average water flow velocity, and the flow velocity is a function of flow estimation.

Calculation results of each parameter to be solved are shown in Table 2:

| Parameter to be solved | | mean | SD | MC error (%) | 2.50% | median | 97.50% |
|---|---|---|---|---|---|---|---|
| TN export coefficient (kg · ha$^{-1}$ · year$^{-1}$) | Garden | 34.58 | 0.88 | 0.39 | 34.58 | 34.58 | 18.62 |
| | Dry land | 64.87 | 0.40 | 0.17 | 64.17 | 64.87 | 65.45 |
| | Paddy field | 20.29 | 0.41 | 0.17 | 19.79 | 20.29 | 21.10 |
| | Woodland | 8.60 | 0.25 | 0.30 | 8.10 | 8.60 | 9.87 |
| | Residential land | 42.95 | 0.38 | 0.17 | 41.25 | 42.95 | 43.66 |
| | k | 0.18 | 0.12 | 0.16 | 0.05 | 0.18 | 0.40 |

Further, an amount of non-point source pollutants entering the river for each of different landscape types in the watershed is calculated.

That is, by application of the determined export coefficient value and k, with reference to different land-use structure in Hengxi watershed, the amount of TN entering the river for each landscape type from year 2015 to year 2019 is calculated. A map showing percentages of TN entering the river for different land-use types is obtained, as shown in FIG. 12.

It can be seen from FIG. 12 and Table 2 that in the case of the Hengxi watershed, although the woodland has a smaller export coefficient, compared with other land-use types, the woodland has the greatest contribution to the impact of non-point source pollution in the watershed, which was mainly related to a relatively large area proportion of the woodland and a spatial distribution pattern thereof in the watershed. Therefore, the traceability analysis of non-point source pollution needs to take into account not only the export coefficient of pollutants from pollution sources, but also the area of the pollution sources and the whole process of pollutants migrated to the river after being discharged.

According to the amount of the non-point source pollutants entering the river which is obtained through inverse traceability with the constructed pollution traceability model, the priority of each non-point source pollution area can be quickly determined at the watershed scale, and a key area in which non-point source pollution needs to be controlled can be accurately anchored according to the priority. Thus, the targeted governance work can be carried out on the key areas by concentrated resources and manpower, thereby improving governance effectiveness. Based on the amount of the non-point source pollutants entering the river, corresponding non-point source control strategies can be designed, such as adjusting agricultural fertilization plans to improve urban drainage systems. Furthermore, application rates of agricultural chemicals such as pesticides and fertilizers can be controlled through intelligent irrigation systems based on the amount of the non-point source pollutants entering the river. Alternatively, an alarm mechanism can be designed so that in response to the amount of the non-point source pollutants entering the river exceeding a predetermined threshold, an alarm or an annunciator can be automatically activated to send an alert to a user for taking corresponding means.

It can be understood that in the method for traceability of non-point source pollution in a watershed according to the embodiment of the present disclosure, a method for dealing with spatial heterogeneity of landscape elements in landscape ecology is applied to a non-point source pollution traceability model, so as to establish a non-point source pollution traceability model based on landscape patterns and the non-point source pollution process, which is conductive to accurately obtain parsing results of non-point source pollution sources in the watershed, quantitatively evaluate an amount of non-point source pollutants entering the river for different landscape types in the watershed, and effectively identify key pollution sources of non-point source pollution in the watershed, thereby providing effective guidance for control of non-point source pollution in the watershed, and having the characteristics of easy data acquisition and higher accuracy of obtained results, and the like.

In another aspect, an embodiment of the present disclosure further provides an apparatus for inverse traceability of non-point source pollution in a watershed. The apparatus includes an acquiring module, a first determining module, and a second determining module.

The acquiring module is configured to acquire basic data of a studied watershed, where the basic data includes a digital elevation map, a land-use type map, hydrologic data, water quality data, and a weight and prior data of an export coefficient of each landscape type in the studied watershed, the landscape type includes a source landscape and a sink landscape, where the source landscape represents a landscape type that acts as a pollution source in the studied watershed, and the sink landscape represents a landscape type that acts as a sink for pollutants in the studied watershed.

The first determining module is configured to determine an LWLI of each landscape type in the studied watershed and a pollutant load of the studied watershed in a predetermined time cycle according to the basic data, where the LWLI is used to indicate an impact of each landscape pattern on a migration process of non-point source pollutants, and the pollutant load includes a pollutant load exported from the non-point source pollution to an outlet section of the studied watershed.

The second determining module is configured to determine, according to the pollutant load and the LWLI, based on a pre-constructed pollution traceability model, an amount of the non-point source pollutants entering the river for each landscape type in the studied field, where the amount of the non-point source pollutants entering the river for each landscape type in the studied field represents an amount of pollutants exported by each landscape type and entering the river and is used to measure a contribution of each landscape type to non-point source pollution in the studied watershed.

In some embodiments, in the apparatus for inverse traceability of non-point source pollution in the watershed according to the embodiment of the present disclosure, the first determining module is specifically configured to:

calculate a relative distance-based LWLI, a relative elevation-based LWLI and a slope-based LWLI according to the basic data; and fuse the calculated relative distance-based LWLI, relative elevation-based LWLI and slope-based LWLI to obtain the LWLI.

In some embodiments, in the apparatus for inverse traceability of non-point source pollution in the watershed according to the embodiment of the present disclosure, the first determining module is specifically configured to:

determine, according to the digital elevation map and a land-use type, an area of each landscape type under a relative distance, a relative elevation or a slope, and a cumulative percentage of the area;

determine a Lorenz curve corresponding to each landscape type according to the cumulative percentage of the area; and determine the relative distance-based LWLI, the relative elevation-based LWLI and the slope-based LWLI based on the determined Lorenz curve and the weight.

In some embodiments, in the apparatus for inverse traceability of non-point source pollution in the watershed according to the embodiment of the present disclosure, the first determining module is specifically configured to:

calculate by means of a following formula:

$$LWLI_{Relative\ distance/relative\ elevation/slope} = \frac{\sum_{i=1}^{m} A_{Sourcei} \times w_i \times AP_i}{\sum_{j=1}^{n} A_{Sinkj} \times w_j \times AP_j},$$

where m represents a total number of source landscapes in the studied watershed; n represents a total number of sink landscapes in the studied watershed; $A_{Source\ i}$ and $A_{Sink\ i}$ represent areas enclosed by Lorenz curves of an $i^{th}$ source landscape and a $j^{th}$ sink landscape in the studied watershed, respectively, and $AP_i$ and $AP_j$ represent area percentages of the $i^{th}$ source landscape and the $j^{th}$ sink landscape in the watershed, respectively; and $w_i$ and $w_j$ represent weights of the $i^{th}$ source landscape and the $j^{th}$ sink landscape, respectively.

In some embodiments, in the apparatus for inverse traceability of non-point source pollution in the watershed according to the embodiment of the present disclosure, the first determining module is specifically configured to:

use a quotient obtained by dividing a product of the relative distance-based LWLI and the relative elevation-based LWLI by the slope-based LWLI as the LWLI.

In some embodiments, in the apparatus for inverse traceability of non-point source pollution in the watershed according to the embodiment of the present disclosure, the pre-constructed pollution traceability model is as follows:

$$NS_g = \sum_{\eta=1}^{m+n}\left(\frac{f(Q_g)}{f(\overline{Q})}\right)e^{\eta}A_{\eta}LWLI\exp\left(-k\frac{T_g}{2}\right),$$

where $NS_g$ represents a pollutant load exported from a non-point source to the outlet section of the studied watershed in a $g^{th}$ time cycle; $\eta$ represents a number of land-use types, with a total of m+n; $\overline{Q}$ represents an average runoff flow rate in a predetermined time cycle; $Q_g$ represents a runoff flow rate in the $g^{th}$ time cycle; $f(\ )$ represents a functional relationship between a runoff flow rate at an outlet of the studied watershed and a pollutant load in runoff; $e^{\eta}$ represents a pollutant export coefficient of a $\eta^{th}$ land-use type; $A_{\eta}$ represents an area of the $\eta^{th}$ land-use type; a subscript g represents a $g^{th}$ time cycle; and k represents a first-order kinetic loss rate constant of river pollutants.

In some embodiments, in the apparatus for inverse traceability of non-point source pollution in the watershed according to the embodiment of the present disclosure, the second determining module is specifically configured to:

determine, according to the pollutant load and the LWLI, based on the pre-constructed pollution traceability model, parameter to be determined in the pollution traceability model by using a Bayesian inversion algorithm, where the parameter to be determined includes a pollutant export coefficient corresponding to each land-use type and a first-order kinetic loss rate constant of river pollutants; and determine an amount of non-point source pollutants entering the river for each land-use type in the studied field according to the pollutant export coefficient corresponding to each land-use type.

In some embodiments, in the apparatus for inverse traceability of non-point source pollution in the watershed according to the embodiment of the present disclosure, the second determining module is specifically configured to:

use a product of a pollutant export coefficient corresponding to each land-use type and the area, the LWLI and a runoff correction coefficient as an amount of non-point source pollutants entering the river for each land-use type.

In some embodiments, in the apparatus for inverse traceability of non-point source pollution in the watershed according to the embodiment of the present disclosure, the first determining module is specifically configured to:

determine the pollutant load of the studied watershed in the predetermined time cycle according to the basic data by using a LOADEST model.

In yet another aspect, an embodiment of the present disclosure provides a computer device. The computer device further includes a memory, a processor, and a computer program stored in the memory and executable on the processor, where the processor, when executing the computer program, implements the method for inverse traceability of non-point source pollution in the watershed described above.

Figure 13:
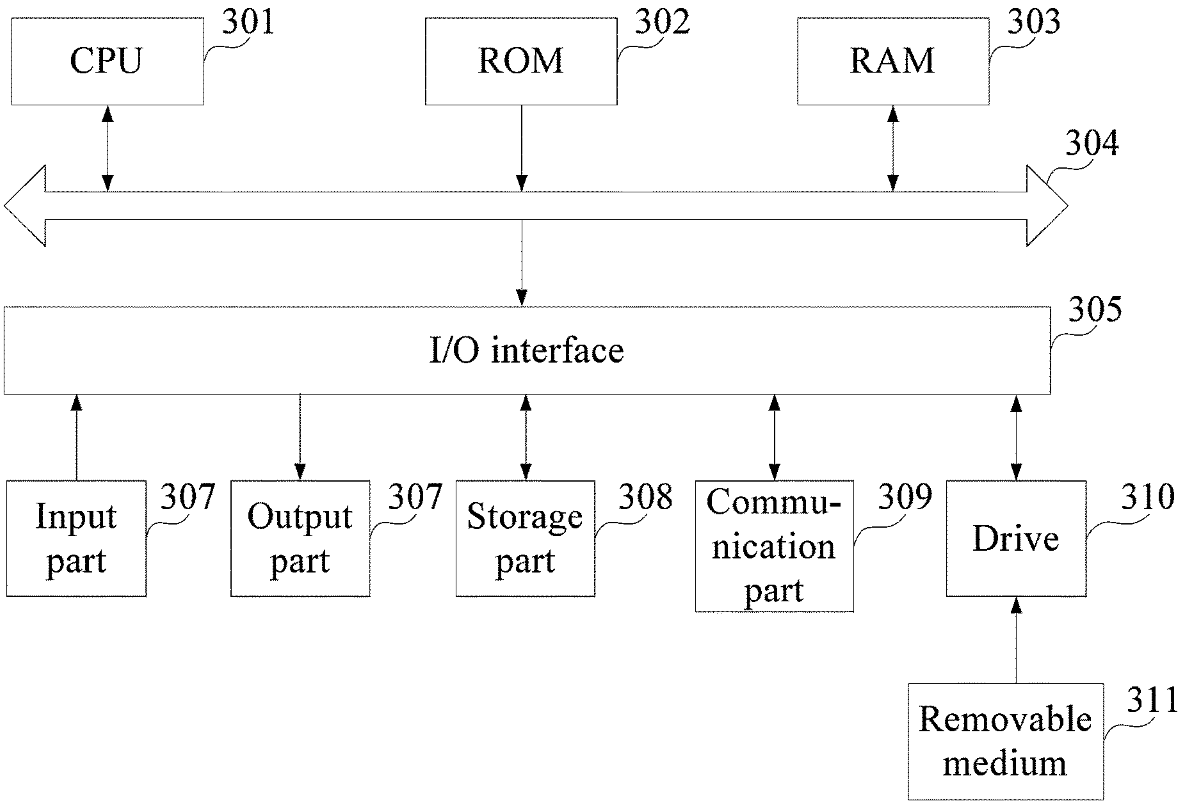
FIG. 13 is a schematic structural diagram of a computer device according to an embodiment of the present disclosure.

Referring to FIG. 13, FIG. 13 is a schematic structural diagram of a computer device according to an embodiment of the present disclosure.

As shown in FIG. 13, an electronic device includes a central processing unit (CPU) 301, which can perform various suitable actions and processing according to a program stored in a read-only memory (ROM) 302 or a program loaded from a storage part 308 to a random access memory (RAM) 303. The RAM 303 further stores various programs and data required for operations of the electronic device 300. The CPU 301, the ROM 302, and the RAM 303 are connected to one another by means of a bus 304. An input/output (I/O) interface 305 is also connected to the bus 304. In some embodiments, the following components are connected to the I/O interface 305: an input part 306 including a keyboard, a mouse, and the like; an output part 307 including a cathode-ray tube (CRT), a liquid crystal display (LCD), a loudspeaker, and the like; a storage part 308 including a hard disk and the like; and a communication part 309 including a network interface card such as a local area network (LAN) card or a modem. The communication part 309 performs communication processing via a network such as the Internet. A drive 310 is also connected to the I/O interface 305 as needed. A removable medium 311, such as a magnetic disc, an optical disk, a magneto-optical disk, or a semiconductor memory, is mounted on the drive 310 as needed, such that a computer program read therefrom is installed into the storage part 308 as needed. Particularly, according to the embodiments of the present disclosure, the process described above with reference to the flowchart may be implemented as a computer software program. For example, an embodiment of the present disclosure includes a computer program product including a computer program carried by a computer-readable medium. The computer program includes program code for executing the method shown in the flowchart. In such an embodiment, the computer program may be downloaded and installed from the network by means of the communication part 309, and/or may be installed from the removable medium 311. When the computer program is executed by the CPU 301, the aforementioned functions defined in the electronic device of the present disclosure are performed.

It should be noted that, the computer-readable medium in the present disclosure may be a computer-readable signal medium, a computer-readable storage medium, or a combination thereof. The computer-readable storage medium may be, for example, but is not limited to, electrical, magnetic, optical, electromagnetic, infrared, or semiconductor electronic equipment or apparatuses or devices, or any combination thereof. More specific examples of the computer-readable storage medium may include, but are not limited to: an electrical connector with one or more wires, a portable computer magnetic disk, a hard disk, an RAM, an ROM, an erasable programmable read-only memory (EPROM or flash memory), an optical fiber, a compact disc read-only memory (CD-ROM), an optical storage device, a magnetic storage device, or any proper combination thereof. In the present disclosure, the computer-readable storage medium may be any tangible medium that contains or stores a program, and the program may be used by or in combination with an instruction-executing electronic equipment, apparatus, or device. In the present disclosure, the computer-readable signal medium may include a data signal propagated in a baseband or as a part of a carrier, and computer-readable program code is carried therein. The propagated data signal may be in various forms, including but not limited to an electromagnetic signal, an optical signal, or any suitable combination thereof. The computer-readable signal medium may alternatively be any computer-readable medium other than the computer-readable storage medium. The computer-readable medium may send, propagate or transmit a program used by or in combination with an instruction-executing electronic equipment, apparatus, or device. The program code contained on the computer-readable medium may be transmitted using any suitable medium, including but not limited to: wireless, a wire, an optical fiber, radio frequency (RF), or any suitable combination thereof.

The flowcharts and block diagrams in the accompanying drawings illustrate architectures, functions, and operations of possible implementations of the electronic device, method, and computer program product according to various embodiments of the present disclosure. Each block in the flowcharts or block diagrams may represent a module, a program segment, or a part of code, and the module, the program segment, or the part of code contains one or more executable instructions used to implement specified logical functions. It should also be noted that, in some alternative implementations, the functions marked in the blocks may alternatively occur in a different order from that marked in the accompanying drawings. For example, two successively shown blocks actually may be executed in parallel substantially, or may be executed in reverse order sometimes, depending on the functions involved. It should also be noted that each block in the block diagrams and/or the flowcharts and a combination of the blocks in the block diagrams and/or the flowcharts may be implemented by a dedicated hardware-based electronic device for executing specified functions or operations, or may be implemented by a combination of dedicated hardware and computer instructions.

The units or modules described in the embodiments of the present disclosure may be implemented in a form of software or in a form of hardware. The describe units or modules may alternatively be disposed in a processor, and this, for example, may be described as follows: A processor includes an acquisition module, a first determining module, and a second determining module. The names of these units or modules in some cases do not constitute the limitation of the unit or module itself. For example, the first determining module may be further described as "configured to determine an LWLI of each landscape type in the studied watershed and a pollutant load of the studied watershed in a predetermined time cycle according to the basic data, where the LWLI is used to indicate an impact of each landscape pattern on a migration process of non-point source pollutants, and the pollutant load includes a pollutant load exported from a non-point source pollution to an outlet section of the studied watershed."

In yet another aspect, the present disclosure further provides a computer-readable storage medium. The computer-readable storage medium may be contained in the electronic device described in the foregoing embodiment, or may exist alone without being assembled in the electronic device. The computer-readable storage medium stores one or more computer programs, and the computer programs are used by one or more processors to perform the method for inverse traceability of non-point source pollution in a studied watershed according to the present disclosure, which includes:

acquiring basic data of a studied watershed, where the basic data includes a digital elevation map, a land-use type map, hydrologic data, water quality data, and a weight and prior data of an export coefficient of each landscape type in the studied watershed, the landscape type includes a source landscape and a sink landscape, where the source landscape represents a landscape type that acts as a pollution source in the studied watershed, and the sink landscape represents a landscape type that acts as a sink for pollutants in the studied watershed;

determining an LWLI of each landscape type in the studied watershed and a pollutant load of the studied watershed in a predetermined time cycle according to the basic data, where the LWLI is used to indicate an impact of each landscape pattern on a migration process of non-point source pollutants, and the pollutant load includes a pollutant load exported from the non-point source pollution to an outlet section of the studied watershed; and determining, according to the pollutant load and the LWLI, based on a pre-constructed pollution traceability model, an amount of the non-point source pollutants entering the river for each landscape type in the studied field, where the amount of the non-point source pollutants entering the river for each landscape type in the studied field represents an amount of pollutants exported by each landscape type and entering the river and is used to measure a contribution of each landscape type to non-point source pollution in the studied watershed.

To sum up, in the method for inverse traceability of non-point source pollution in the watershed and the computer device according to the present disclosure, during the process of tracing a source of non-point source pollution in a studied watershed, basic data in the studied watershed is acquired first, then an LWLI of each landscape type in the studied watershed and a pollutant load of the studied watershed in a predetermined time cycle are determined by means of the acquired basic data, and then according to the determined LWLI and pollutant load, an amount of pollutants entering a river, which represents a contribution of each landscape type to non-point source pollution in the studied watershed, is solved based on a pre-constructed pollution traceability model. That is, in the present disclosure, the determined LWLI included in the pollution traceability model can show an impact of each landscape pattern on a migration process of non-point source pollutants, and thus determined parameters are used to solve parameters in the pollution traceability model, which is conductive to accurately acquire parsing results of non-point source pollution sources in the watershed, quantitatively evaluate an amount of non-point source pollutants entering the river for different landscape types in the watershed, and effectively identify key pollution sources of non-point source pollution in the watershed, thereby providing effective guidance for control of non-point source pollution in the watershed, and having the characteristics of easy data acquisition, and higher accuracy of obtained results, and the like. Therefore, the failure to fully consider the impact of a watershed landscape spatial structure on the non-point source pollution process in related technologies is avoided, and quantitative traceability of non-point source pollution in the watershed is achieved.

The above description is merely an illustration of preferred embodiments of the present disclosure and the technical principle in use. Those skilled in the art should understand that, the disclosure scope described in the present disclosure is not limited to the technical solution formed by a specific combination of the foregoing technical features, but should cover other technical solutions formed by any combination of the foregoing technical features or equivalent features thereof without departing from the foregoing disclosure concept. For example, a technical solution is formed by replacing the foregoing feature with a technical feature having a similar function disclosed in (but not limited to) the present disclosure.

What is claimed is:

1. A method for inverse traceability of non-point source pollution in a watershed, comprising:

acquiring basic data of a studied watershed, wherein the basic data comprises a digital elevation map, a land-use type map, hydrologic data, water quality data, and a weight and prior data of an export coefficient of each landscape type in the studied watershed, the landscape type comprises a source landscape and a sink landscape, wherein the source landscape represents a landscape type that acts as a pollution source in the studied watershed, and the sink landscape represents a landscape type that acts as a sink for pollutants in the studied watershed;

determining a location-weighted landscape contrast index (LWLI) of each landscape type in the studied watershed and a pollutant load of the studied watershed in a predetermined time cycle according to the basic data, wherein the LWLI is used to indicate an impact of each landscape pattern on a migration process of non-point source pollutants, and the pollutant load comprises a pollutant load exported from the non-point source pollution to an outlet section of the studied watershed;

determining, according to the pollutant load and the LWLI, based on a pre-constructed pollution traceability model, an amount of the non-point source pollutants entering a river for each landscape type in the studied field, wherein the amount of the non-point source pollutants entering the river for each landscape type in the studied field represents an amount of pollutants exported by each landscape type and entering the river and is used to measure a contribution of each landscape type to non-point source pollution in the studied watershed; and determining whether the amount of the non-point source pollutants entering the river exceeds a predetermined threshold, and sending a single to an external device in response to a determination that the amount of the non-point source pollutants entering the river exceeds a predetermined threshold.

2. The method according to claim 1, wherein the determining an LWLI of each landscape type in the studied watershed according to the basic data comprises:

calculating a relative distance-based LWLI, a relative elevation-based LWLI and a slope-based LWLI according to the basic data; and fusing the calculated relative distance-based LWLI, relative elevation-based LWLI and slope-based LWLI to obtain the LWLI.

3. The method according to claim 2, wherein the calculating a relative distance-based LWLI, a relative elevation-based LWLI and a slope-based LWLI according to the basic data comprises:

determining, according to the digital elevation map and a land-use type, an area of each landscape type under corresponding distance, relative elevation or slope, and a cumulative percentage of the area;

determining a Lorenz curve corresponding to each landscape type according to the cumulative percentage of the area; and determining the relative distance-based LWLI, the relative elevation-based LWLI and the slope-based LWLI based on the determined Lorenz curve and the weight.

4. The method according to claim 3, wherein the determining the relative distance-based LWLI, the relative elevation-based LWLI and the slope-based LWLI based on the determined Lorenz curve and the weight comprises:

calculating by means of a following formula:

$$LWLI_{Relative\ distance/relative\ elevation/slope} = \frac{\sum_{i=1}^{m} A_{Sourcei} \times w_i \times AP_i}{\sum_{j=1}^{n} A_{Sinkj} \times w_j \times AP_j},$$

where m represents a total number of source landscapes in the studied watershed; n represents a total number of sink landscapes in the studied watershed; $A_{Source\ i}$ and $A_{Sink\ i}$ represent areas enclosed by Lorenz curves of an $i^{th}$ source landscape and a $j^{th}$ sink landscape in the studied watershed, respectively, and $AP_i$ and $AP_j$ represent area percentages of the $i^{th}$ source landscape and the $j^{th}$ sink landscape in the watershed, respectively; and $w_i$ and $w_j$ represent weights of the $i^{th}$ source landscape and the $j^{th}$ sink landscape, respectively.

5. The method according to claim 3, wherein the fusing the calculated relative distance-based LWLI, relative elevation-based LWLI and slope-based LWLI to obtain the LWLI comprises:

using a quotient obtained by dividing a product of the relative distance-based LWLI and the relative elevation-based LWLI by the slope-based LWLI as the LWLI.

6. The method according to claim 2, wherein the pre-constructed pollution traceability model is:

$$NS_g = \sum_{\eta=1}^{m+n} \left( \frac{f(Q_g)}{f(\overline{Q})} \right) e^{\eta} A_{\eta} LWLI \exp\left( -k \frac{T_g}{2} \right),$$

where $NS_g$ represents a pollutant load exported from a non-point source to the outlet section of the studied watershed in a $g^{th}$ time cycle; η represents a number of land-use types, with a total of m+n; $\overline{Q}$ represents an average runoff flow rate in a predetermined time cycle; $Q_g$ represents a runoff flow rate in the $g^{th}$ time cycle; $f(\ )$ represents a functional relationship between a runoff flow rate at an outlet of the studied watershed and a pollutant load in runoff; $e^{\eta}$ represents a pollutant export coefficient of a $\eta^{th}$ land-use type; $A_{\eta}$ represents an area of the $\eta^{th}$ land-use type; a subscript g represents a $g^{th}$ time cycle; and k represents a first-order kinetic loss rate constant of river pollutants.

7. The method according to claim 6, wherein the determining, according to the pollutant load and the LWLI, based on a pre-constructed pollution traceability model, an amount of the non-point source pollutants entering the river for each landscape type in the studied field comprises:

determining, according to the pollutant load and the LWLI and based on the pre-constructed pollution traceability model, parameter to be determined in the pollution traceability model by using a Bayesian inversion algorithm, wherein the parameter to be determined comprises a pollutant export coefficient corresponding to each land-use type; and determining an amount of non-point source pollutants entering the river for each land-use type in the studied field according to the pollutant export coefficient corresponding to each land-use type.

8. The method according to claim 6, wherein the determining an amount of non-point source pollutants entering a river for each land-use type in the studied field according to the pollutant export coefficient corresponding to each land-use type comprises:

using a product of a pollutant export coefficient corresponding to each land-use type and the area, the LWLI and a runoff correction coefficient as an amount of non-point source pollutants entering the river for each land-use type.

9. The method according to claim 2, wherein the determining a pollutant load of the studied watershed in a predetermined time cycle according to the basic data comprises:

determining the pollutant load of the studied watershed in the predetermined time cycle according to the basic data by using a LOADEST model.

10. The method according to claim 1, wherein the external device is an annunciator, which issues a warming in response to receiving the signal.

11. The method according to claim 1, wherein the external device is an irrigation system, which, in response to receiving the signal, adjusts application rates of agricultural chemicals based on the amount of the non-point source pollutants entering the river.

12. A computer device, comprising a memory, a processor, and a computer program stored in the memory and executable on the processor, wherein the processor, when executing the computer program, implements the method for inverse traceability of non-point source pollution in the watershed according to claim 1.

13. The computer device according to claim 12, wherein the determining an LWLI of each landscape type in the studied watershed according to the basic data comprises:

calculating a relative distance-based LWLI, a relative elevation-based LWLI and a slope-based LWLI according to the basic data; and fusing the calculated relative distance-based LWLI, relative elevation-based LWLI and slope-based LWLI to obtain the LWLI.

14. The computer device according to claim 13, wherein the calculating a relative distance-based LWLI, a relative elevation-based LWLI and a slope-based LWLI according to the basic data comprises:

determining, according to the digital elevation map and a land-use type, an area of each landscape type under corresponding distance, relative elevation or slope, and a cumulative percentage of the area;

determining a Lorenz curve corresponding to each landscape type according to the cumulative percentage of the area; and determining the relative distance-based LWLI, the relative elevation-based LWLI and the slope-based LWLI based on the determined Lorenz curve and the weight.

15. The computer device according to claim 14, wherein the determining the relative distance-based LWLI, the relative elevation-based LWLI and the slope-based LWLI based on the determined Lorenz curve and the weight comprises:

calculating by means of a following formula:

$$LWLI_{Relative\ distance/relative\ elevation/slope} = \frac{\sum_{i=1}^{m} A_{Sourcei} \times w_i \times AP_i}{\sum_{j=1}^{n} A_{Sinkj} \times w_j \times AP_j},$$

where m represents a total number of source landscapes in the studied watershed; n represents a total number of sink landscapes in the studied watershed; $A_{Source\ i}$ and $A_{Sink\ i}$ represent areas enclosed by Lorenz curves of an $i^{th}$ source landscape and a $j^{th}$ sink landscape in the studied watershed, respectively, and $AP_i$ and $AP_j$ represent area percentages of the $i^{th}$ source landscape and the $j^{th}$ sink landscape in the watershed, respectively; and $w_i$ and $w_j$ represent weights of the $i^{th}$ source landscape and the $j^{th}$ sink landscape, respectively.

16. The computer device according to claim 14, wherein the fusing the calculated relative distance-based LWLI, relative elevation-based LWLI and slope-based LWLI to obtain the LWLI comprises:

using a quotient obtained by dividing a product of the relative distance-based LWLI and the relative elevation-based LWLI by the slope-based LWLI as the LWLI.

17. The computer device according to claim 13, wherein the pre-constructed pollution traceability model is:

$$NS_g = \sum_{\eta=1}^{m+n}\left(\frac{f(Q_g)}{f(\overline{Q})}\right)e^{\eta}A_{\eta}LWLI\exp\left(-k\frac{T_g}{2}\right),$$

where $NS_g$ represents a pollutant load exported from a non-point source to the outlet section of the studied watershed in a $g^{th}$ time cycle; $\eta$ represents a number of land-use types, with a total of m+n; $\overline{Q}$ represents an average runoff flow rate in a predetermined time cycle; $Q_g$ represents a runoff flow rate in the $g^{th}$ time cycle; $f(\ )$ represents a functional relationship between a runoff flow rate at an outlet of the studied watershed and a pollutant load in runoff; $e^{\eta}$ represents a pollutant export coefficient of a $\eta^{th}$ land-use type; $A_{\eta}$ represents an area of the $\eta^{th}$ land-use type; a subscript g represents a $g^{th}$ time cycle; and k represents a first-order kinetic loss rate constant of river pollutants.

18. The computer device according to claim 17, wherein the determining, according to the pollutant load and the LWLI, based on a pre-constructed pollution traceability model, an amount of the non-point source pollutants entering the river for each landscape type in the studied field comprises:

determining, according to the pollutant load and the LWLI and based on the pre-constructed pollution traceability model, parameter to be determined in the pollution traceability model by using a Bayesian inversion algorithm, wherein the parameter to be determined comprises a pollutant export coefficient corresponding to each land-use type; and determining an amount of non-point source pollutants entering the river for each land-use type in the studied field according to the pollutant export coefficient corresponding to each land-use type.

19. The computer device according to claim 17, wherein the determining an amount of non-point source pollutants entering a river for each land-use type in the studied field according to the pollutant export coefficient corresponding to each land-use type comprises:

using a product of a pollutant export coefficient corresponding to each land-use type and the area, the LWLI and a runoff correction coefficient as an amount of non-point source pollutants entering the river for each land-use type.

20. The computer device according to claim 13, wherein the determining a pollutant load of the studied watershed in a predetermined time cycle according to the basic data comprises:

determining the pollutant load of the studied watershed in the predetermined time cycle according to the basic data by using a LOADEST model.

* * * * *